US009080157B2

(12) United States Patent
Convents et al.

(10) Patent No.: US 9,080,157 B2
(45) Date of Patent: Jul. 14, 2015

(54) PRODUCTS COMPRISING INACTIVATED YEASTS OR MOULDS AND ACTIVE VHH-TYPE ANTIBODIES

(75) Inventors: Daniel Convents, Vlaardingen (NL); Leo G. Frenken, Vlaardingen (NL); Michael M. Harmsen, Amsterdam (NL); Richard H. van der Linden, Almere (NL); Cornelis T. Verrips, Vlaardingen (NL)

(73) Assignee: BAC IP B.V., Naarden (NL)

( * ) Notice: Subject to any disclaimer, the term of this patent is extended or adjusted under 35 U.S.C. 154(b) by 0 days.

(21) Appl. No.: 13/462,262

(22) Filed: May 2, 2012

(65) Prior Publication Data
US 2012/0309054 A1 Dec. 6, 2012

Related U.S. Application Data

(62) Division of application No. 09/623,995, filed as application No. PCT/EP99/01678 on Mar. 12, 1999.

(30) Foreign Application Priority Data

Mar. 12, 1998 (EP) ..................................... 98104479
Feb. 16, 1999 (EP) ..................................... 99200439

(51) Int. Cl.
| | | |
|---|---|---|
| *A61K 49/16* | (2006.01) | |
| *A61K 39/40* | (2006.01) | |
| *C12Q 1/68* | (2006.01) | |
| *C12P 21/08* | (2006.01) | |
| *C12P 19/34* | (2006.01) | |
| *C12N 1/16* | (2006.01) | |
| *A23L 1/305* | (2006.01) | |
| *A61K 8/64* | (2006.01) | |
| *A61Q 5/02* | (2006.01) | |
| *A61Q 15/00* | (2006.01) | |
| *A61Q 19/00* | (2006.01) | |
| *A61Q 19/10* | (2006.01) | |
| *C07K 1/14* | (2006.01) | |
| *C11D 17/00* | (2006.01) | |
| *C12N 1/14* | (2006.01) | |
| *C07K 16/00* | (2006.01) | |
| *C07K 16/12* | (2006.01) | |

(52) U.S. Cl.
CPC ................ *C12N 1/16* (2013.01); *A23L 1/3058* (2013.01); *A61K 8/64* (2013.01); *A61Q 5/02* (2013.01); *A61Q 15/00* (2013.01); *A61Q 19/00* (2013.01); *A61Q 19/10* (2013.01); *C07K 1/14* (2013.01); *C07K 16/00* (2013.01); *C07K 16/1232* (2013.01); *C11D 17/006* (2013.01); *C12N 1/14* (2013.01); *A61K 2800/52* (2013.01); *A61K 2800/70* (2013.01)

(58) Field of Classification Search
None
See application file for complete search history.

(56) References Cited

U.S. PATENT DOCUMENTS

| | | |
|---|---|---|
| 4,600,706 A | 7/1986 | Carter |
| 4,877,615 A | 10/1989 | Vandenbergh et al. |
| 5,433,947 A | 7/1995 | Harman et al. |
| 5,585,098 A | 12/1996 | Coleman |
| 5,627,072 A | 5/1997 | Leenhouts et al. |
| 5,989,584 A | 11/1999 | Cook et al. |
| 6,033,705 A | 3/2000 | Isaacs |
| 6,068,862 A | 5/2000 | Ishihara et al. |
| 6,120,732 A | 9/2000 | Toledo et al. |
| 6,165,776 A | 12/2000 | Eklund |

FOREIGN PATENT DOCUMENTS

| | | |
|---|---|---|
| EP | 0739981 | 10/1996 |
| EP | 0899326 | 9/2003 |
| WO | 94/18330 | 8/1994 |
| WO | 94/25591 | 11/1994 |
| WO | 94/29457 | 12/1994 |

OTHER PUBLICATIONS

Harmsen et al (Appl. Gen. Mol. Biotech., published online Feb. 1, 2006).*
van der Linden et al., "Comparison of physical chemical properties of llama VHH antibody fragments and mouse monoclonal antibodies." Biochim et Biophys Acta 1431: 37-46, 1999.
Merriam-Webster Online Dictionary. medical.merriam-webster.com/medical/chaotropic, Jun. 16, 2008.
Sci-Tech Dictionary. ansers.com/topic/chaotropic-biochemistry, Jun. 16, 2008.
EverythingBio. everythingbio.com/glos/definition.php?ID=3453, Jun. 16, 2008.
Transue et al., "Camel single-domain antibody inhibits enzyme by mimicking carbohydrate substrate." Proteins: Structure, Function and Genetics 32: 515-522, 1998.
Frenken et al., "Recent advances in the large-scale production of antibody fragments using lower eukaryotic microorganisms." Res. Immunol. 149: 589-599, 1998.
Montijano et al., "Assessment of nehesperidine DC stability during pasteurization of juice-based drinks." Int. J. Food Sci. Techn. 31: 397-401, 1996.
Humeau et al., "Effect of Sugar, Stabilizing Agents, Acids and Potassium Sorbate on the Thermal Inactivation of *Saccharomyces cerevisiae* in a Food Product." Microbiologie-Ailments-Nutrition 15: 123-130, 1997.
Qin et al., "Nonthermal Pasteurization of Liquid foods Using High-Intensity Pulsed Electric Fields." Crit. Rev. Food Sci. Nutr. 36: 603-627, 1996.
MSN Encarta Dictionary. encarta.msn.com/encnet/features/dictionary/DibtionaryResults.aspx?refid=1861710272, 2 pages, 2006.
Davies et al., "Single antibody domains as small recognition units: design and in vitro antigen selection of camelized, human Vh domains with improved protein stability." Protein Eng. 9: 531-537, 1996.
Roitt et al., Immunology, Gower Med. Pub., London/New York, p. 6.2, col. 2, figure 8.6, 1985.
Butkus et al., CABI Accession No. 78: 23046 CABA, 1976.

(Continued)

*Primary Examiner* — Gerald R Ewoldt
*Assistant Examiner* — Marianne Dibrino
(74) *Attorney, Agent, or Firm* — MH2 Technology Law Group, LLP

(57) ABSTRACT

The use of VHHs in the preparation of products to provide stability of antibody specificity under destabilizing conditions whereby normally lower eukaryotes or traditional antibodies are killed or inactivated.

17 Claims, 8 Drawing Sheets

(56) References Cited

OTHER PUBLICATIONS

Edwards-Ingram et al., "Genotypic and Physiological Characterization of *Saccharomyces boulardii*, the Probiotic Strain of *Saccharomyces cerevisiae*," Appl Environ Microbiol., 73(8): 2458-2467 (2007).

Henning, S. et al. "Studies on the mode of action of nisin". International Journal of Food Microbiology vol. 3, Mar. 24, 1985, pp. 121-134.

Ohkawa, M. et al. "Clinical Significance of the Antibody-coated Bacteria Test in Patients with Candiduria", British Journal of Urology, vol. 66, Jan. 29, 1990, pp. 22-25.

Penley, C. et al. "Inhibition of Fungi by Soft Contact Lens Solutions as Determined by FDA-Recommended Tests", Dev. Ind. Microbiol., vol. 24, 1983, pp. 369-375.

Schreuder, M. et al. "Immobilizing proteins on the surface of yeast cells", TIBTECH, vol. 14., 1996, pp. 115-120.

Spinelli, et al. "The crystal structure of a llama heavy", Nature Structural Biology, vol. 3 (9), Sep. 1996, pp. 752-757.

Taiwar, P. et al. "Standardization and of antibody-coated candida in urine by direct", Mycopathologia, vol. 94, 1986, pp. 39-44.

Harmsen, M. et al. "Selection and optimization of proteolytically stable llama single-domain antibody fragments for oral immunotherapy", Applied Genetics and Molecular Biotechnology, Applied Microbiology and Biotechnology, Springer-Verlag, Feb. 1, 2006. 23 pages.

\* cited by examiner

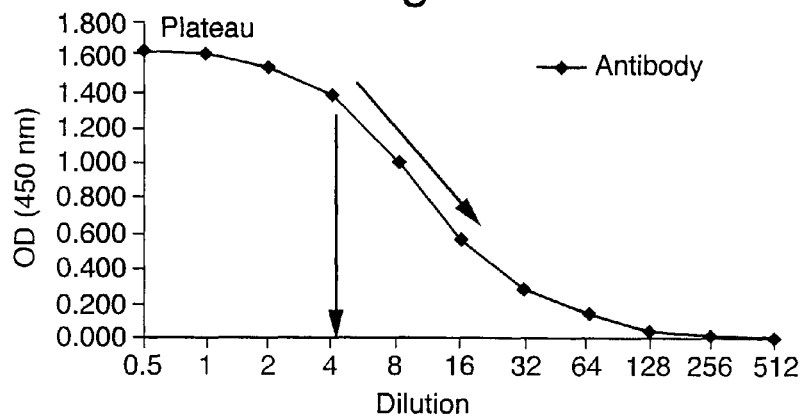
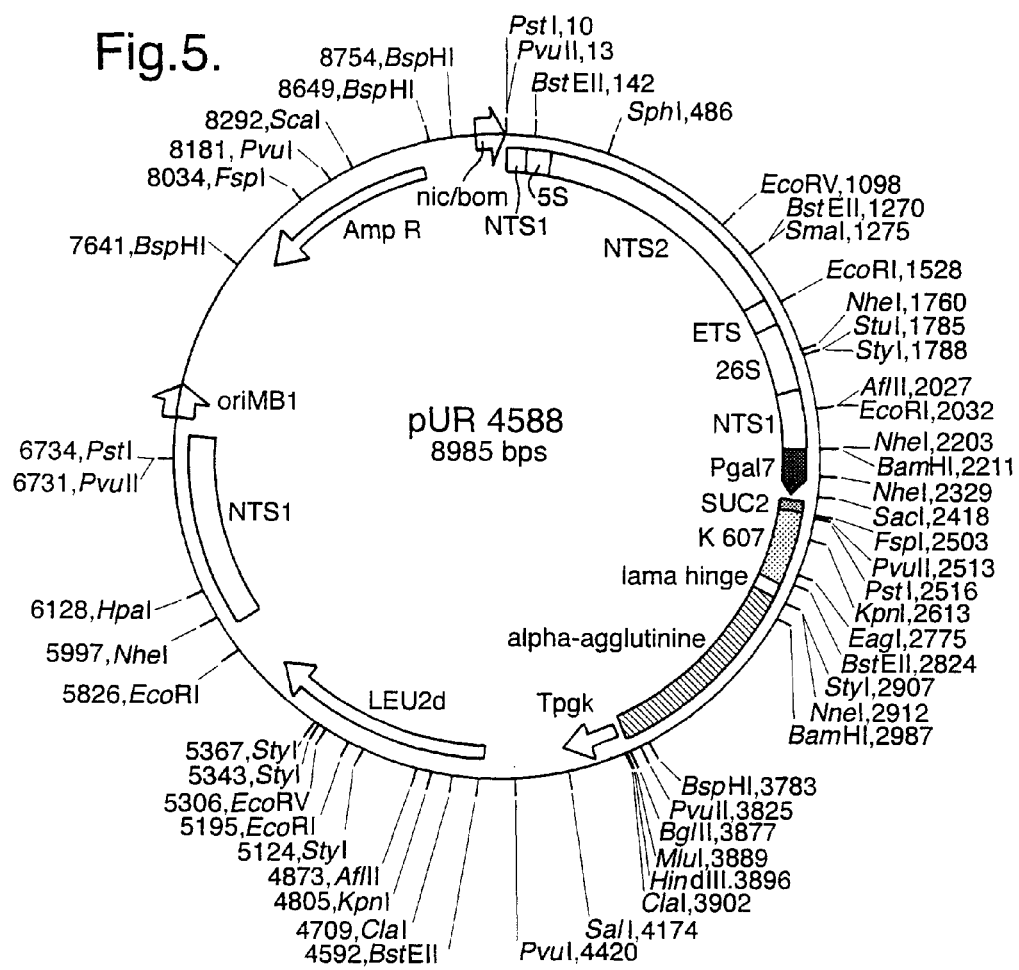

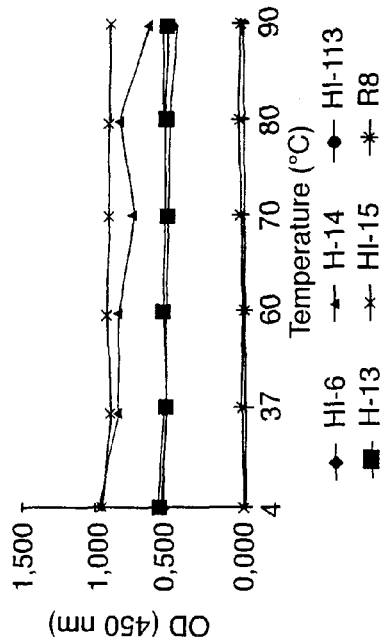
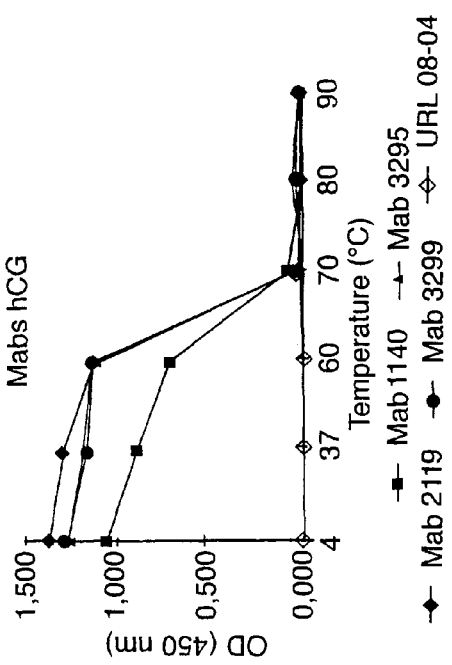
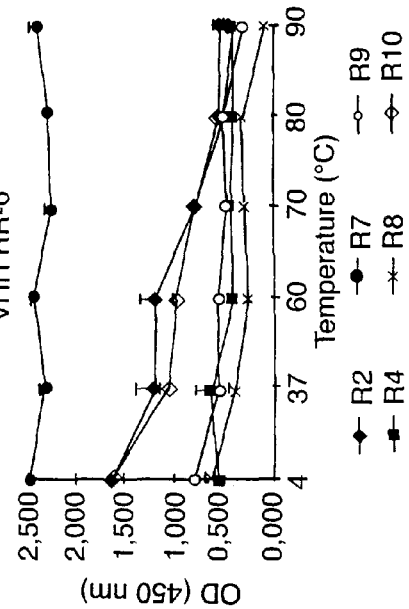
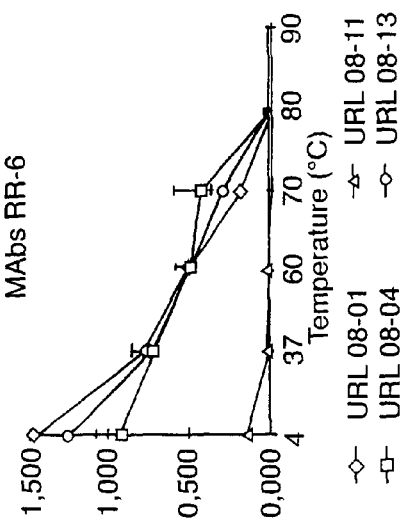

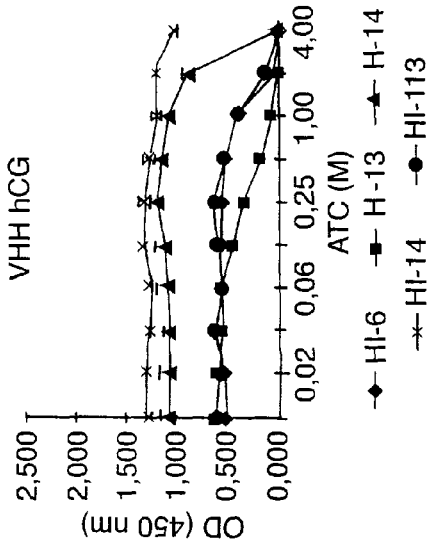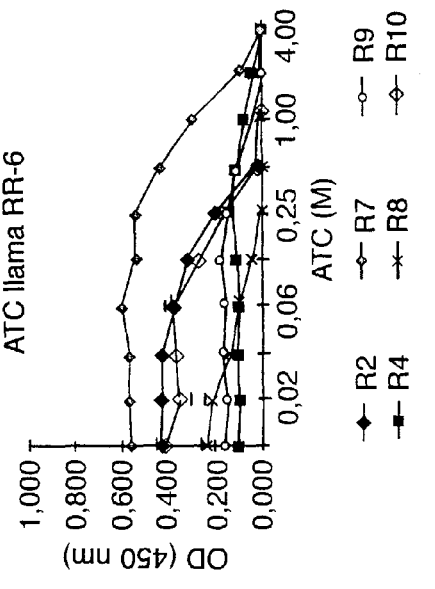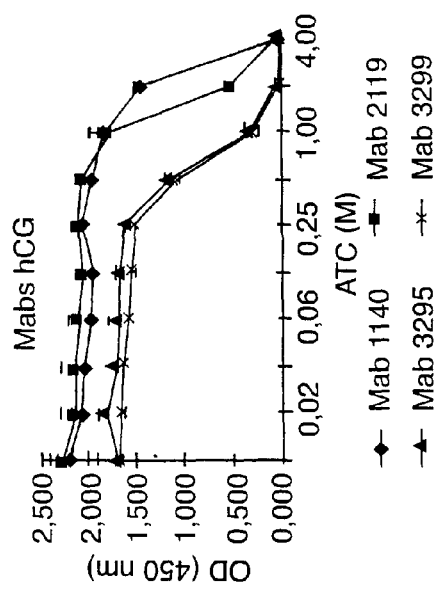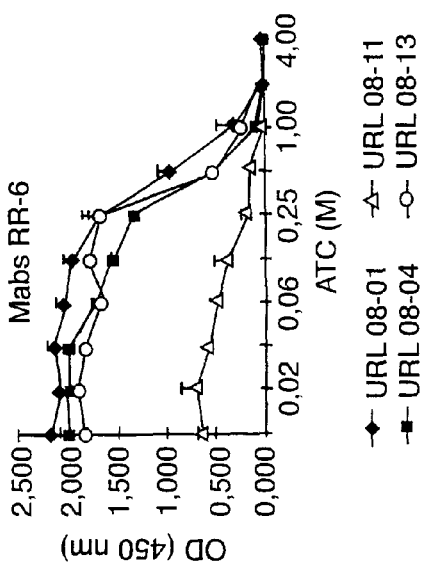

Fig.10.

```
           frame I                              cdr I      frame II
                  10        20        30                        40
           ....|....|....|....|....|....|       ....|      ....|....|....
RR120_38   QVQLQESGGGLVQAGDSLRLSCEASGPTFS        RYAFG      WFRQTPGQEREFVG
RR120_44   QVQLQESGGGLVHAGGSLRLSCAASGRIFR        IDSMA      WYRQTPGKQRELVA
RR120_306  QVQLQESGGGLVQAGGSLRLSCVASGNDFS        IYDIG      WYRQAPGKPREFVA
RR120_307  QVQLQESGGGLVQAGDSLRLSCVASGNDFS        IYDIG      WYRQAPGNPREFVA
RR120_308  QVQLQESGGGLVQAGGSLRLSCVASGNDFS        IYDIG      WYRQAPGKPREYVA
RR120_309  QVQLQQSGGGVVHAGGSLRLSCVASGRIFR        IDEMS      WHRQTPGKQRELVA cdr II                       frame III
           50           60              70        80        90
           |..ab..|....|....|           ....|....|....|....|..abc..|....
RR120_38   AMTWRGGLTSVVADSVKG           RFTIFRDMTRNMMWLQMNDLKAGDSAVYYCAA
RR120_44   TIT--DGGMTNYADSVRG           RFTISRDGAKNTVYLQMNILKPEDTAVYYCNA
RR120_306  AIG--RGGYTNIDASVKG           RFTISRDNAKNTVYLQMDTLKPEDTAVYSCAA
RR120_307  AIG--RGGYTNIDASVKG           RFTISRDNAKNTVYLQMNTLKPEDTAVYSCAA
RR120_308  AVG--KGGYTNIAASVKG           RFTISRDNAKNTVYLQMNTLKPEDTAVYSCAA
RR120_309  SMS--IDGVAKYADSVKG           RFTISRDNAKNTVYLQMNFLKHEDTAVYYCNA cdr III                      frame IV
               100                         110
           |....|abcdefghi..             ..|....|...
RR120_38   RPRGSLYYSEDSY--DY             WGQGTQVTVSS
RR120_44   RGPYSRGS-------GP             WGQGTQVTVSS
RR120_306  AKRYGSGRLDDITRYNY             WGQGTQVTVSS
RR120_307  AQRYGPGRLNDISRYNY             WGQGTQVTVSS
RR120_308  AERYGSGRLGDITRYSY             WGHGTQVTVSS
RR120_309  RGPYSRGS-------GP             WGQGTQVTVSS
```

```
                          SEQUENCE LISTING

<160> NUMBER OF SEQ ID NOS: 35

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
aggtsmarct gcagsagtcw gg                                            22

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 2
aacagttaag cttccgcttg cggccgcgga gctggggtct tcgctgtggt gcg          53

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 3
aacagttaag cttccgcttg cggccgctgg ttgtggtttt ggtgtcttgg gtt          53

<210> SEQ ID NO 4
<211> LENGTH: 5
<212> TYPE: PRT
```

<213> ORGANISM: Lama glama

<400> SEQUENCE: 4

Gln Val Gln Leu Gln
 1               5

<210> SEQ ID NO 5
<211> LENGTH: 6
<212> TYPE: PRT
<213> ORGANISM: Lama glama

<400> SEQUENCE: 5

Gln Val Thr Val Ser Ser
 1               5

<210> SEQ ID NO 6
<211> LENGTH: 111
<212> TYPE: PRT
<213> ORGANISM: Lama glama

<400> SEQUENCE: 6

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Ser Ile Phe Ser Ala Ser
            20                  25                  30

Ala Met Thr Trp Tyr Arg Gln Ala Pro Gly Lys Ser Arg Glu Tyr Val
        35                  40                  45

Ala Arg Ile Phe Phe Ser Gly Gly Thr Asn Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Asp Leu Lys Arg Glu Asp Thr Ala Val Tyr Tyr Cys Asn
                85                  90                  95

Leu Leu Ser Tyr Trp Gly Gln Gly Thr Gln Val Thr Val Ser Ser
            100                 105                 110

<210> SEQ ID NO 7
<211> LENGTH: 125
<212> TYPE: PRT
<213> ORGANISM: Lama glama

<400> SEQUENCE: 7

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Gly Thr Phe Ser Trp Tyr
            20                  25                  30

Ala Met Gly Trp Phe Arg Gln Ala Pro Gly Lys Glu Arg Glu Phe Val
        35                  40                  45

Ala Thr Val Ser Arg Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Gly Arg Gly Ser Pro Ser Asp Thr Gly Arg Pro Asp Glu Tyr
            100                 105                 110

Asp Tyr Trp Gly Gln Gly Thr Gln Val Thr Val Ser Ser
        115                 120                 125

```
<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 8
ggtatggatc cacrtccacc accacrcayg tgacct                              36

<210> SEQ ID NO 9
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (2)..(61)

<400> SEQUENCE: 9 g gtc acc gtc tcc tca gcg cac cac agc gaa gac ccc agc tcc aag tgt    49
  Val Thr Val Ser Ser Ala His His Ser Glu Asp Pro Ser Ser Lys Cys
  1               5                   10                  15 ccc aaa tgc cca                                                      61
Pro Lys Cys Pro
            20

<210> SEQ ID NO 10
<211> LENGTH: 103
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (2)..(103)

<400> SEQUENCE: 10 g gtc acc gtc tcc tca gaa ccc aag aca cca aaa cca caa cca caa cca    49
  Val Thr Val Ser Ser Glu Pro Lys Thr Pro Lys Pro Gln Pro Gln Pro
  1               5                   10                  15 caa cca caa cca caa ccc aat cct aca aya gaa tcc aag tgt ccc aag      97
Gln Pro Gln Pro Gln Pro Asn Pro Thr Thr Glu Ser Lys Cys Pro Lys
            20                  25                  30 tgt cca                                                             103
Cys Pro

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 11
cgcggctagc cttggattct gttgtaggat tgggttg                             37

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 12
```
cccaggtcac cgtctcctca gaacccaag                                              29

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (1)..(33)

<400> SEQUENCE: 13 cct aca aca gaa tcc aag tgt ccc aag tgt cca                                  33
Pro Thr Thr Glu Ser Lys Cys Pro Lys Cys Pro
 1               5                  10

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (1)..(24)

<400> SEQUENCE: 14 cct aca aca gaa tcc aag gct agc                                              24
Pro Thr Thr Glu Ser Lys Ala Ser
 1               5

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
ggaattcgtc tcctcagaac aaaaac                                                 26

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
gctgctgcaa aaggaattta                                                        20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
aaattccttt tgcagcagc                                                         19

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

```
<400> SEQUENCE: 18
gggaagcttc gacaaaagca gaaaaatga                                29

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 19
ttacaaaagt gggttcttca gatggaa                                  27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 20
ttccatctga agaacccact tttgtaa                                  27

<210> SEQ ID NO 21
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (1)..(45)

<400> SEQUENCE: 21 gag ctg ggt tcg atc att ttt ctg ctt ttg tcg tac ctg cta ttc    45
Glu Leu Gly Ser Ile Ile Phe Leu Leu Leu Ser Tyr Leu Leu Phe
 1               5                  10                  15 taagatctga ttaaacgcgt gaagctt                                  72

<210> SEQ ID NO 22
<211> LENGTH: 150
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgcaggagt cataatgagg gacccaggtc accgtctcct cagcggccgc aagcggaagc    60
ttagaacaaa aactcatctc agaagaggat ctgaatgggg ccgcacatca ccatcatcac   120
catggggccg catagagctt aactgttgaa                                   150

<210> SEQ ID NO 23
<211> LENGTH: 125
<212> TYPE: PRT
<213> ORGANISM: Artificial Sequence
<220> FEATURE:
<223> OTHER INFORMATION: Description of Artificial Sequence: Mutagen

<400> SEQUENCE: 23

Gln Val Gln Leu Gln Glu Ser Gly Gly Gly Leu Val Gln Ala Gly Asp
 1               5                  10                  15

Ser Leu Arg Leu Ser Cys Glu Ala Ser Gly Pro Thr Phe Ser Arg Tyr
```

```
            20                  25                  30
Ala Phe Gly Trp Phe Arg Gln Thr Pro Gly Gln Glu Arg Glu Phe Val
            35                  40                  45

Gly Ala Met Thr Trp Arg Gly Gly Leu Thr Ser Val Ala Asp Ser
        50                  55                  60

Val Lys Gly Arg Phe Thr Ile Phe Arg Asp Met Thr Arg Asn Met Met
 65                  70                  75                  80

Trp Leu Gln Met Asn Asp Leu Lys Ala Gly Asp Ser Ala Val Tyr Tyr
                85                  90                  95

Cys Ala Ala Arg Pro Arg Gly Ser Leu Tyr Tyr Ser Glu Asp Ser Tyr
                100                 105                 110

Asp Tyr Trp Gly Gln Gly Thr Gln Val Thr Val Ser Ser
            115                 120                 125

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Mutagen

<400> SEQUENCE: 24

Gln Val Gln Leu Gln Glu Ser Gly Gly Gly Leu Val His Ala Gly Gly
  1               5                  10                  15

Ser Leu Arg Leu Ser Cys Ala Ala Ser Gly Arg Ile Phe Arg Ile Asp
            20                  25                  30

Ser Met Ala Trp Tyr Arg Gln Thr Pro Gly Lys Gln Arg Glu Leu Val
            35                  40                  45

Ala Thr Ile Thr Asp Gly Gly Met Thr Asn Tyr Ala Asp Ser Val Arg
        50                  55                  60

Gly Arg Phe Thr Ile Ser Arg Asp Gly Ala Lys Asn Thr Val Tyr Leu
 65                  70                  75                  80

Gln Met Asn Ile Leu Lys Pro Glu Asp Thr Ala Val Tyr Tyr Cys Asn
                85                  90                  95

Ala Arg Gly Pro Tyr Ser Arg Gly Ser Gly Pro Trp Gly Gln Gly Thr
                100                 105                 110

Gln Val Thr Val Ser Ser
            115

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Mutagen

<400> SEQUENCE: 25

Gln Val Gln Leu Gln Glu Ser Gly Gly Gly Leu Val Gln Ala Gly Gly
  1               5                  10                  15

Ser Leu Arg Leu Ser Cys Val Ala Ser Gly Asn Asp Phe Ser Ile Tyr
            20                  25                  30

Asp Ile Gly Trp Tyr Arg Gln Ala Pro Gly Lys Pro Arg Glu Phe Val
            35                  40                  45

Ala Ala Ile Gly Arg Gly Gly Tyr Thr Asn Ile Asp Ala Ser Val Lys
        50                  55                  60

Gly Arg Phe Thr Ile Ser Arg Asp Asn Ala Lys Asn Thr Val Tyr Leu
 65                  70                  75                  80
```

```
Gln Met Asp Thr Leu Lys Pro Glu Asp Thr Ala Val Tyr Ser Cys Ala
                85                  90                  95

Ala Ala Lys Arg Tyr Gly Ser Gly Arg Leu Asp Asp Ile Thr Arg Tyr
            100                 105                 110

Asn Tyr Trp Gly Gln Gly Thr Gln Val Thr Val Ser Ser
        115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Mutagen

<400> SEQUENCE: 26

Gln Val Gln Leu Gln Glu Ser Gly Gly Gly Leu Val Gln Ala Gly Asp
 1               5                  10                  15

Ser Leu Arg Leu Ser Cys Val Ala Ser Gly Asn Asp Phe Ser Ile Tyr
            20                  25                  30

Asp Ile Gly Trp Tyr Arg Gln Ala Pro Gly Asn Pro Arg Glu Phe Val
        35                  40                  45

Ala Ala Ile Gly Arg Gly Gly Tyr Thr Asn Ile Asp Ala Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Lys Pro Glu Asp Thr Ala Val Tyr Ser Cys Ala
                85                  90                  95

Ala Ala Gln Arg Tyr Gly Pro Gly Arg Leu Asn Asp Ile Ser Arg Tyr
            100                 105                 110

Asn Tyr Trp Gly Gln Gly Thr Gln Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Description of Artificial Sequence: Mutagen

<400> SEQUENCE: 27

Gln Val Gln Leu Gln Glu Ser Gly Gly Gly Leu Val Gln Ala Gly Gly
 1               5                  10                  15

Ser Leu Arg Leu Ser Cys Val Ala Ser Gly Asn Asp Phe Ser Ile Tyr
            20                  25                  30

Asp Ile Gly Trp Tyr Arg Gln Ala Pro Gly Lys Pro Arg Glu Tyr Val
        35                  40                  45

Ala Ala Val Gly Lys Gly Gly Tyr Thr Asn Ile Ala Ala Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Lys Pro Glu Asp Thr Ala Val Tyr Ser Cys Ala
                85                  90                  95

Ala Ala Glu Arg Tyr Gly Ser Gly Arg Leu Gly Asp Ile Thr Arg Tyr
            100                 105                 110

Ser Tyr Trp Gly His Gly Thr Gln Val Thr Val Ser Ser
        115                 120                 125

<210> SEQ ID NO 28
```

```
<211> LENGTH: 118
<212> TYPE: PRT
<213> ORGANISM: Artificial Sequence
<220> FEATURE:
<223> OTHER INFORMATION: Description of Artificial Sequence: Mutagen

<400> SEQUENCE: 28
```

Gln Val Gln Leu Gln Gln Ser Gly Gly Gly Val Val His Ala Gly Gly
 1               5                  10                  15

Ser Leu Arg Leu Ser Cys Val Ala Ser Gly Arg Ile Phe Arg Ile Asp
            20                  25                  30

Glu Met Ser Trp His Arg Gln Thr Pro Gly Lys Gln Arg Glu Leu Val
        35                  40                  45

Ala Ser Met Ser Ile Asp Gly Val Ala Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Phe Leu Lys His Glu Asp Thr Ala Val Tyr Tyr Cys Asn
                85                  90                  95

Ala Arg Gly Pro Tyr Ser Arg Gly Ser Gly Pro Trp Gly Gln Gly Thr
            100                 105                 110

Gln Val Thr Val Ser Ser
        115

```
<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Val Thr Val Ser Ser Ala His His Ser Glu Asp Pro Ser Ser Lys Cys
 1               5                  10                  15

Pro Lys Cys Pro
            20

```
<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Val Thr Val Ser Ser Glu Pro Lys Thr Pro Lys Pro Gln Pro Gln Pro
 1               5                  10                  15

Gln Pro Gln Pro Gln Pro Asn Pro Thr Thr Glu Ser Lys Cys Pro Lys
            20                  25                  30

Cys Pro

```
<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

-continued

```
Pro Thr Thr Glu Ser Lys Cys Pro Lys Cys Pro
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Thr Thr Glu Ser Lys Ala Ser
1               5

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<221> NAME/KEY: CDS
<222> LOCATION: (1)..(33)

<400> SEQUENCE: 33 gag ctc ggt tcg atc att ttt ctg ctt ttg tcg aagctt              39
Glu Leu Gly Ser Ile Ile Phe Leu Leu Leu Ser
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Leu Gly Ser Ile Ile Phe Leu Leu Leu Ser
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Leu Gly Ser Ile Ile Phe Leu Leu Leu Ser Tyr Leu Leu Phe
1               5                   10                  15
```

US 9,080,157 B2

PRODUCTS COMPRISING INACTIVATED YEASTS OR MOULDS AND ACTIVE VHH-TYPE ANTIBODIES

RELATED APPLICATIONS

The present application is a Divisional of U.S. application Ser. No. 09/623,995, filed Apr. 30, 2001, which is a U.S. National Phase Application of International Application No. PCT/EP99/01678, filed Mar. 12, 1999, which claims the benefit of European Patent Application No. 98104479, filed Mar. 12, 1998, and European Patent Application No. 99200439, filed Feb. 16, 1999, all of which are hereby incorporated by reference in their entireties.

FIELD OF THE INVENTION

The present invention is in the field of applied biotechnology and relates in particular to an economic way of introducing antibodies into a variety of products, especially consumer product such as food products and personal care products and animal feed.

BACKGROUND OF THE INVENTION

To fulfil many unmet demands of the society, there is a clear need to provide new products from which consumers may benefit, in particular in the field of food products including animal feed and personal care products such as laundry detergents, deodorants etc. One of the problems with the presently used consumer products is that if they contain functional compounds, these compounds are often not very specific.

For instance, for killing microorganisms in food products the functional compound may be a salt or an acid. If the concentration of either of these compounds is sufficiently high, they are able to kill microorganisms. However, often the level of salt renders the taste of the product less attractive to the consumer. Moreover, high levels of salt are not recommended by health authorities. The same holds for products that contain considerable amounts of acids or preservatives.

Non-food consumer products such as personal care products e.g. laundry detergent products may contain compounds that are able to bleach stains, but as they do not specifically recognise stains, considerable amounts of these bleach generating compounds (e.g. percarbonate/TAED) are necessary.

Another example is that some hair care products contain compounds that kill the microorganisms involved in dandruff. Also these compounds are not specific and in addition to the causative microorganisms of dandruff they also kill other microorganisms on the skin which are beneficial to the consumer.

Still another example of an unmet demand of the society is the overproduction of manure due to cattle farming. Part of this problem is that the conversion of animal feed into nutrients is not optimal due to the presence of negative compounds like phytic acid.

The above given examples of unmet consumer needs and society needs can be extended, but it will already be clear that consumer products and animal feed with compounds which specifically meet the demand of the consumer or society will be of great importance.

The main characteristic of processes in living cells or living species is that they are often highly specific. Enzymes only recognise specific substrates and the specificity of antibodies is unsurpassed. Therefore in recent years the industries involved in the manufacturing of (chemical and biotechnological) consumer products or animal feed are increasingly applying biological molecules in order to make their products more specific.

A successful example of this development is the introduction of proteases, lipases, cellulases and amylases in laundry products. These enzymes have a certain specificity and because the production of these enzymes has been improved considerably by recombinant DNA techniques, these microbial enzymes can be produced by microorganisms at costs affordable for consumer products. The introduction of enzymes in detergents has indeed met demands of our society. Over the last decades the energy usage for cleaning of laundry has been reduced with about 50% and the amount of chemicals with about 40%.

In the area of animal feed enzymes can play an important role to reduce the environmental pollution, as has been nicely demonstrated by the application of the enzyme phytase in animal feed. Again this development was possible due to the enormous improvement of the production of phytase by rDNA techniques.

However, often a higher specificity than just recognising a protein or fat is highly desirable to fulfil the unmet demands and therefore the consumer goods and animal feed industry is looking for ways to get specificities in the same order as antibodies have.

In nature microorganisms do not produce antibodies. Although it is well known that by using rDNA technology microorgansims can produce almost any protein, irrespective of its origin, the yield of homologous proteins is much higher than for heterologous proteins. Moreover, expensive purification processes are needed to recover the heterologous protein from its producing cell, since it is not allowed to bring living rDNA organisms into the environment. These two factors, the low production yield and the fact that rDNA organisms have to be separated from the products that they produce have slowed down the introduction of heterologous proteins in consumer products other than in laundry products and some food products. In animal feed only the addition of phytase is a real success up to now.

The present invention relates in particular to introducing certain categories of antibodies into a variety of products, especially food products, personal care products and animal feed.

Hamers-Casterman et al., *Nature* (1993) 363:446-448 disclose isolated immunoglobulins from the serum of *Camelidae* comprising two heavy polypeptide chains sufficient for the formation of a complete antigen binding site, which immunoglobulins further being devoid of light polypeptide chains.

WO 94/25591 discloses the production of antibodies or functionalised fragments thereof derived from heavy chain immunoglobulins of *Camelidae*, using transformed lower eukaryote host organisms.

Spinelli et al., *Nature structural biology* (1996) 3:752-757 disclose the crystal structure of a llama heavy chain variable domain.

In many processes involving recombinant DNA techniques and culturing or fermenting transformed microorganisms, it is necessary at some stage, for example at the conclusion of the fermentation, to kill the active cells in order to prevent any viable recombinant organisms from being released into the environment.

A conventional way of killing cells is using heat. U.S. Pat. No. 4,601,986 is an example of the use of heat to kill the cells and stop the growth of microorganism cultures. Other conventional ways of killing cells are by lysing the cells, for example by applying high osmotic pressures or by adding enzymes which break down the cell walls or membranes. These techniques are exemplified in U.S. Pat. Nos. 4,299,858, 3,816,260, 3,890,198, and 3,917,510.

In many systems host microorganisms, for example lower eukaryote cells, are difficult to kill. Conventional methods, such as heat, are too severe and may destroy or alter the desired product before the cells are killed. This applies also for the immobilized systems of binding proteins on lower eukaryotes disclosed in WO 94/18330, when the binding protein is an antibody or a functional fragment thereof.

It is often desirable to manufacture, store or use products under conditions which would normally be detrimental to the stability of biological systems such as microorganisms or antibodies. For example products may desirably be heated, e.g. pasteurised during manufacture or use (e.g. high temperature washing) or its composition and/or pH may be such that the biological systems do not survive storage over prolonged periods.

Similarly, there is still a need for stable functional systems possibly involving microorganisms, where the microorganisms are inactivated or killed and/or their growth is surpressed while the functional activity of the system is substantially maintained.

In this light there is a need to use components in products, especially consumer products, whereby on the one hand said components have a acceptable or even good specificity and on the other hand are stable under conditions of manufacture and/or storage and/or use.

BRIEF DESCRIPTION OF TERMS

As used herein, the term "antibody" refers to an immunoglobulin which may be derived from natural sources or may be synthetically produced, in whole or as antibody fragment.

An "antibody fragment" is a portion of a whole antibody which retains the ability to exhibit antigen binding activity. Functionalized antibody fragments are also embraced in this term.

The term "functionalized antibody fragment" is used for indicating an antibody or fragment thereof to which one or more functional groups, including enzymes and other binding polypeptides, are attached resulting in fusion products of such antibody fragment with another biofunctional molecule.

The term "traditional antibody" is used for an antibody which normally consists of two heavy and two light chains or fragments thereof.

The term "VHH" refers to the single heavy chain variable domain antibodies of the type that can be found in Camelid mammals which are naturally devoid of light chains; synthetic and naive VHH can be construed accordingly.

SUMMARY OF THE INVENTION

In one aspect the present invention relates to a method of preparing, storing or using a product comprising active antibodies, wherein said method involves the application of conditions whereby normally lower eukaryotes or traditional antibodies are killed or inactivated and whereby the active antibodies are VHHs.

In another aspect the invention relates to the use of VHHs in the preparation of products to provide stability of antibody specificity under conditions whereby normally lower eukaryotes or traditional antibodies are killed or inactivated.

These and other aspects of the invention will be described in further detail in the description which follows.

BRIEF DESCRIPTION OF THE FIGURES

FIG. 1 shows a typical dilution curve for the antibodies used, from which the sub-saturation point was determined.

FIG. 2 shows the antigen binding after temperature treatment of hCG specific mouse MAbs (A) and llama $V_{HH}s$ (B) or RR-6 specific mouse MAbs (C) and llama $V_{HH}s$ (D). Antibodies were incubated for 2 hrs at different temperatures, cooled down to room temperature and subsequently ELISA was performed.

FIG. 3 shows the antigen binding in presence of ammonium thiocyanate at sub saturation point of hCG specific mouse MAbs (A) and llama $V_{HH}s$ (B) or RR-6 specific mouse MAbs (C) and llama $V_{HH}s$ (D).

FIG. 5 represents a restriction map of plasmid pUR 4588.

FIG. 10 shows the amino acid sequence of anti-RR120 VHHs A38 (SEQ ID:NO 23) and A44 (SEQ ID:NO 24) (obtained by screening in PBS), A306 (SEQ ID:NO 25), A307 (SEQ ID:NO 26) and A308 (SEQ ID:NO 27) (obtained by screening in LAS) and A309 (obtained by screening in Dutch Omo without protease; SEQ ID:NO 28).

DETAILED DESCRIPTION OF THE INVENTION

Figure 4:
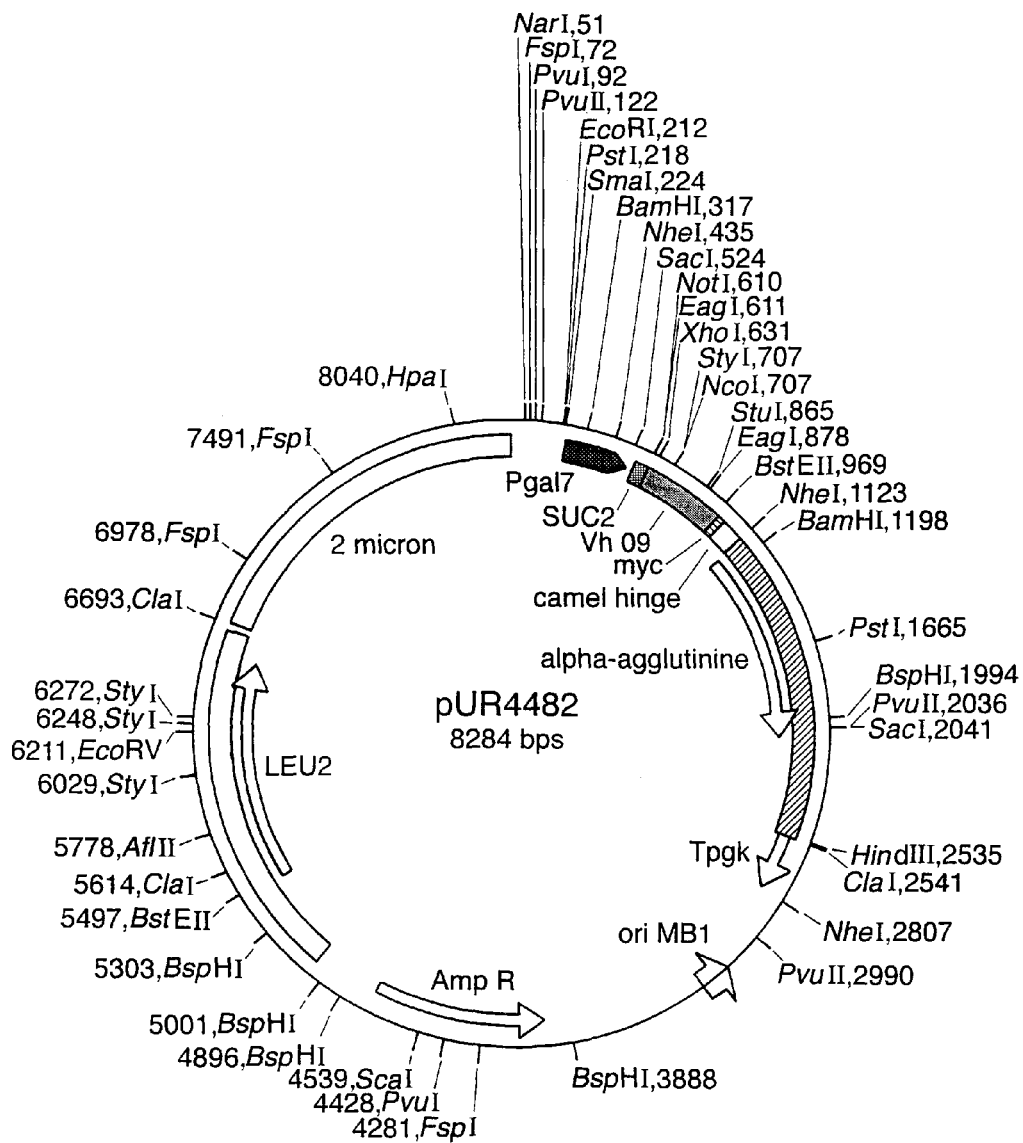
FIG. 4 represents a restriction map of plasmid pUR 4482

Traditional antibodies, consisting of two heavy and two light chains are rather stable when they circulate in the blood and lymph systems to protect the host against invaders. This stability is caused by several S-S bridges between the heavy chains and the strong interaction between the heavy and the light chain. However, production of complete antibodies in microorganisms is very difficult and economically not yet feasible for introduction into consumer products or animal feed.

Recently, it has been shown that antibody fragments of traditional antibodies can be produced by certain microorganisms, but in general the yield of these fragments is rather low. The stability of fragments of traditional antibodies is rather low and the physics of protein stability is still not sufficiently developed to predict protein stability from its amino acid sequence.

The present invention is based on the surprising finding, after extensive research and experimentation, that on average VHHs are more stable against destabilising physical and/or chemical conditions such as one or more of: high temperature, ultra high pressure, pulse electric field, radiation, presence of anti-microbial, presence of (mixed) surfactants, presence of ethanol, pH altering materials and presence of chaotropic agents as compared to eukaryotic cells or as compared to traditional antibodies. It is even more surprising that certain variable domains of Camelidae antibodies from llamas appear to be very stable under pasteurisation conditions.

Therefore in a first aspect the inventions relates to a method of preparing (including the identification of antibodies), storing or using a product comprising active antibodies, wherein said method involves the application of destabilising conditions whereby normally lower eukaryotes or traditional antibodies are killed or inactivated and wherein the active antibodies are VHHs.

In another aspect the invention relates to the use of VHHs in the preparation of products to provide stability of antibody specificity under destabilising conditions whereby normally lower eukaryotes or traditional antibodies are killed or inactivated.

The invention is further based on the finding that physical techniques or chemical treatment, or a combination of physical techniques and chemical treatment or a combination of special types of mild techniques which are destabilising conditions in that they are able to kill or inactivate lower eukaryotes e.g. *Saccharomyces Cerevisiae*. Typically the lower eukaryotes would be reduced by a factor of at least $10^6$, or which are able to kill or inactivate traditional antibodies, surprisingly can be used whereby the VHHs retain their immunoreactivity to a large extent, typically >60%, and preferably from about 70% to 100% or even 90% to 100%.

Preferably the destabilising conditions are such that normally lower eukaryote cells are inactivated with a factor of at least $10^6$. Typically the conditions are chosen such that under these conditions lower eukaryotes would be reduced by a factor of at least $10^6$, because this killing efficiency is often acceptable for the health authorities as killing efficiency for pathogenic bacteria in food products. A preferred reduction is with a factor of $10^7$ to $10^9$. Particularly the conditions are chosen such that the activity of *Saccharomyces cerevisiae* would be reduced by a factor of at least $10^6$.

In a preferred embodiment the destabilising conditions are such that normally the immunoreactivity of traditional antibodies is reduced to less than 70%, more preferred less than 10%, e.g. less than 1% or even less than 0.01%. Typical examples of traditional antibodies are mouse monoclonal antibodies. Especially preferably the destabilising conditions are such that the immunoreactivity of mouse monoclonal antibodies agains hCG as described in Gani M, Coley J and Porter P Hybridoma 6: (6) 637-643, December 1987 (hereafter referred to as HCGMABS) is reduced to less than 70%, more preferred less than 10%, e.g. less than 1% or even less than 0.01%.

The VHHs for use in accordance to the invention are stable under the conditions whereby the lower eukaryotic cells or traditional antibodies are normally killed or substantially inactivated. In particular they preferably recognise their binding target e.g. harmful microorganisms or toxins with a binding constant of $>10^4$, preferably $>10^6$ or $>10^7$, most preferably $>10^6$ and/or retain their immunoreactivity for at least 70%, more preferred from 80-100%, most preferred from 90 to 100% after application of the destabilising conditions for eukaryotic cells and/or traditional antibodies.

The destabilising conditions preferably comprise physical treatments and/or chemical conditions which are applied during manufacture, storage or use of the product.

Suitable examples of physical treatment as destabilising conditions are selected from one or more of:

(a) a high temperature treatment, for example at more than 70° C., for example 80°, 90° or 100° C., especially 70-100° C. The duration of the heat treatment is not very critical but will normally be between 30 seconds and 2 hours, e.g. 1-60 minutes. Preferably the duration is such that on the one hand destabilising conditions are present for lower eukaryotes or traditional antibodies, but on the other hand the VHHs are not substantially deactivated. Typical examples of such conditions are for example pasteurisation of the product during manufacture or use of the product under high temperature conditions e.g. high temperature (e.g. >70° C. washing).

(b) ultra high pressure treatment, for example at 250 Mpa or more, say 250-500 Mpa. Again the duration of the high pressure treatment is not very critical, but will normally be between 1 second and 2 hours, e.g. 1-60 minutes.

(c) irradiation treatment, for example at least 10 kGray gamma radiation, for example 10-50 kGray gamma radiation.

(d) pulse electric field treatment. Suitable application conditions of pulse electric field are well-known in the art.

Optionally physical treatment destabilising conditions can be used in combination with one or more chemical destabilising conditions. If this is done, generally it is possible to use relatively mild physical conditions in combination with relatively mild chemical conditions. In particular it was found that combinations of mild physical treatments and antimicrobial compounds, such as acids or antimicrobial peptides were even more effective to kill the lower eukaryotes, while maintaining the functionality of the VHH. Using these combinations, killing effects of $>10^7$ could be achieved, while the functionality of the antibody remained substantially unaffected.

In another embodiment of the invention the destabilising conditions involve chemical treatment e.g. selected from one or more of:

(a) the presence of an effective amount of antimicrobial agent, for example sorbic acid, benzoic acid, nisin, MB21, or another bacteriocin. Typically the effective amount of antimicrobial agents are chosen such that they are capable to contribute to the destabilising conditions. The exact effective level is usually dependent on the type of agent and the whether or not other destabilising treatments are applied but may normally be from 1 ppm to 5 wt %, e.g. 0.01 to 2 wt %.

(b) the presence of an effective amount of a cell wall degrading enzyme, for example $\beta$-(1,3)-glucanase, $\beta$-(1,6)-glucanase, chitinase and/or a redox enzyme. Typically the effective amount of such enzymes are chosen such that they are capable to contribute to the destabilising conditions. The exact effective level is usually dependant on the type of enzyme and whether or not other destabilising treatments are applied but may normally be from 1 ppm to 1 wt %, e.g. 0.0001 to 0.1 wt %.

(c) the presence of solvent materials e.g. alcohol at for example at a level of at least 10 wt %. These high levels of alcohol are often destabilising especially for lower eukaryotes such as yeasts. Typical destabilising levels for solvent materials may vary in a wide range dependant on the type of solvent and the other destabilising conditions which are applied. Normally levels of 3-96 wt % would be used, e.g. 10 to 35 wt % of the product. A convenient solvent material is ethanol.

(d) the presence of surfactant materials, especially mixtures of two or more surfactants e.g. selected from the group of anionic, nonionic or zwitterionic detergency materials for example at a level of at least 0.2 g/l. Typical examples of suitable surfactant materials are well-known in the art e.g in the formulation of household detergent or personal washing systems such as shampoo. The level of the surfactant materials may vary e.g. between 5 and 50 wt % of the product, e.g. 10-30 wt % or much lower levels such as 0.01 to 20 g/l in the washing solution or the screening medium. Advantageously, mixtures of anionic and nonionic surfactants are used in a weight ratio of from 10:1 to 1:10.

e) the presence of chaotropic materials e.g. ammonium thiocyanate (ATC), urea and/or ATC elution;

(f) the presence of materials e.g. acidifying or buffering materials which render the pH less than 5 or more than 9, examples of these are NaCO3, acetic acid, citric acid etc.

As described above the chemical treatment may advantageously be used in combination with one or more physical treatments.

In accordance to an aspect of the invention the destabilising conditions are applied during one or more of preparation, storage or use of the product. For the purpose of this invention the term "preparation of the product" refers to all steps carried out in the preparation of the product in the presence of VHH such as on the one hand "selection" of the VHH, and on the other hand actual "manufacture" of the product e.g. mixing of ingredients with VHHs, pasteurization, drying, packaging etc.

Surprisingly it has been found that VHHs are often more stable than traditional antibodies. One of the problems in the manufacture of products especially the stage of identification of suitable antibodies for use in products e.g. food, personal care or animal feed products is that the selection is usually done in a model system. The good stability of VHHs now renders it possible to carry out the identification of the effective VHHs under destabilisation conditions. For example the VHHs can be screened in a medium comparable to the product in which the VHH is to be used. For example antibodies for use in personal care products such cleaning formulations e.g. laundry detergents or shampoos can be screened in the product. This is an easy and effective way to identify VHHs which on the one hand have adequate binding affinity towards the target molecule, but which are on the other hand stable under product conditions.

Although applicants have found that VHHs are on average more stable than traditional antibodies or lower eukaryotes, it may still be desirable to apply a selection step to VHHs whereby the VHHs which are most stable under the destabilising conditions are selected. Such a selection step may be carried out by any suitable method, however as described above a preferred method involves the screening of VHHs under product conditions e.g. in the presence of a system which is equal or similar to the product in which the VHH is to be used. Therefore in a preferred embodiment of the invention both the selection of suitable VHHs and at least one further step selected from manufacture, use or storage takes place under destabilising conditions.

Therefore the invention also relates to a method to prepare a product comprising VHHs, comprising the steps of: selection of suitable VHHs by screening under conditions which are equal or similar to the conditions of the product; and incorporating the selected VHHs in the product. Preferably such product is manufactured, used or stored under destabilising conditions for lower eukaryotes or traditional antibodies as described above. The invention also encompasses a product obtainable by such a method.

In another embodiment of the invention, the manufacture of the product involves the combination of ingredients and application of destabilising conditions. For example it is often desirable in the production of a food, personal care or animal feed product to heat the product, e.g. to ensure pasteurisation to ensure keepability. If traditional antibodies are present during such a heating step, they are generally inactivated and hence they can only be added after the pasteurization step, which is clearly less desired. Surprisingly it has been found that VHHs are often more stable against the use of destabilising conditions applied in the manufacturing process of products.

In another embodiment of the invention the storage of the product involves the application of destabilising conditions. For example the chemical composition of the product may contain ingredients which would normally destabilise traditional antibodies and/or eukaryotes. Surprisingly it has been found that VHHs have an enhanced stability wrt said destabilising conditions which renders it possible to store the product for pro-longed periods e.g 1 week to 1 year without an unacceptable reduction of immunoreactivity.

In another embodiment the use of the product involves the application of destabilising conditions. For example the use of a food product may include the heating thereof to temperatures which would normally destabilise lower eukaryotes and/or traditional antibodies. Alternatively personal care products e.g. laundry detergents may be used under high temperature conditions. Surprisingly it has been found that VHHs can be used and retain their stability for the antibody activity when destabilising conditions are applied during use.

Preferred products in which VHHs can be applied include, for example, consumer products. A preferred group of products are food products such as ice-cream, oil based products such as margarines, oils, mayonnaise, dressings, soups, sauces, soft drinks, for example tea based drinks, meals etc. Another preferred group of products are personal care product such as cleaning products like soap bars, washing liquids, gels, laundry detergents e.g. in powder, paste, tablet or liquid form, and deodorants, creams, lotions, shampoo etc. A third group of products are animal feed products in dry or wet form.

Typical amounts of VHHs in the product are from 0.001 µM to 1 M, under the destabilising conditions e.g. in the preparation, storage or use the amounts can typically be from 0.1 to 100 µM, e.g. 2 to 20 µM.

The invention will be illustrated by means of the following examples which also show the use of Mouse monoclonal antibodies.

Mouse monoclonal antibodies (MAbs) or fragments thereof have many potential applications in addition to for example cancer therapy and diagnostic kits. However, for most applications large quantities are needed whereas costs have to be reduced. For MAbs or fragments thereof these conditions often cannot be met. The Camelidae heavy-chain antibodies offer a solution to this problem. Probably because of their simple one chain structure and their solubility (Spinelli et al., 1996), VHHs, especially the variable part of llama heavy chain can be secreted relatively pure and in high amounts by the yeast *S. cerevisiae*. For this reason VHHs, especially llama VHHs are suitable for large scale applications.

As will be shown in the experimental part, VHHs, especially llama VHHs are far more heat stable compared to mouse MAbs. Most VHHa were still able to bind after two hours at temperatures as high as 90° C. The thermal denaturation at lower temperatures of mouse MAbs can be explained because of heavy and light chain separation. After cooling down, these fragments will not associate, or only randomly, resulting substantially in non-functional antibodies.

In general, VHHs and mouse MAbs are comparable in antigen binding in the presence of ATC (ammonium thiocyanate). HCG specific antibodies could bind at higher ATC concentrations than RR-6 specific antibodies. This is probably due to the nature of the antigen and or antibody-antigen interaction.

Regarding the specificity, VHHs have about the same potential as mouse MAbs in recognition of antigen. Within the small subset of anti-hCG, llama $V_{HH}s$, some were found specific to separate alpha-subunit, beta-subunit and intact hCG. The anti-RR6 llama $V_{HH}s$ did not crossreact with other azodyes, resembling RR-6 in structure. The small subset tested seems to be very specific to RR-6.

Most of the VHHs have apparent affinities ($K_D$) range of $10^{-7}$-$10^{-9}$ M, which is of high affinity. Some mouse MAbs used were found to have higher affinity ($10^9$-$10^{11}$ $M^{-1}$) which can be contributed to avidity because mouse MAbs are bivalent.

In summary, when comparing the biochemical properties of VHHs, especially llama VHHs and mouse MAbs for stability, specificity and affinity, it appears that VHHs have physical chemical properties which make them excellent candidates for use both in existing and novel applications. These applications are in a variety of fields and which are immediately evident to the man skilled in the art. As most food products have to be pasteurized, the addition of VHHs create really new options. For example, VHHs that bind and neutralize redox enzymes thereby preventing colour changes of food products, or VHHs that recognize proteins or polysaccharide of food products thereby providing or improving the structure to the product, or VHHs that bind off flavours (scavenging) or bind flavours (controlled release).

The invention is further illustrated by the following experimental work which however is not intended to limit the invention in any respect.

Example I

Materials and Methods

To investigate if VHHs such as llama antibodies can be used in a range of applications, a number of physical chemical and functional characteristics was investigated, thereby concentrating on three characteristics: stability, specificity and affinity. Llama $V_{HH}$s and "classical" bivalent mouse monoclonal IgG antibodies ("mouse Mabs"), specific for either the human pregnancy hormone or the azodye Reactive Red-6 ("RR-6"), were compared with respect to heat stability and antigen binding in chaotropic environment (ammonium thiocyanate (ATC) elution). Furthermore, llama $V_{HH}$s were tested for their antigen specificity and affinity. Both llama and mouse antibodies consist of two subsets: one specific for the protein antigen Chorionic Gonadotropin (hCG) and one specific for the hapten azodye RR-6.

The results show that llama especially regarding functional binding at high temperature (about 90° C.) llama $V_{HH}$s are extraordinarily stable, compared to mouse MAbs.

Example I.1

Purification of Llama $V_{HH}$s and Mouse MAbs

Llama $V_{HH}$s HI-6, H-13, H-14, HI-15, HI-113 (anti-hCG) and R2, R4, R7, R8, R9, R10 (anti RR-6), described in EMBL data library accession numbers: AJ236095 (HI-6), AJ236096 (H-13), AJ236094 (H-14), AJ236097 (HI-15), AJ236098 (HI-113), AJ236100 (R2), AJ236102 (R4), AJ236105 (R7), AJ236106 (R8), AJ236107 (R9), and AJ236108 (R10), were secreted by S. cerevisiae as a fusion protein comprising a $V_{HH}$ with a C-terminal myc-tag and a (H is)-6-tag. For stability studies, yeast culture supernatants containing llama $V_{HH}$s were ultrafiltrated using membranes with cut off limits of 50 kD and 5 kD, respectively, (Filtron, USA) and dialysed against phosphate buffered saline (PBS, 145 mM NaCl, 7.5 mM $Na_2HPO_4$, 2.5 mM $NaH_2PO_4$, 0.01% sodium azide).

The final $V_{HH}$ preparation had a purity between 80-90% as judged by Coomassie Brilliant Blue (R-250, Sigma, Zwijndrecht, the Netherlands) staining of sodium dodecyl sulphate polyacrylamide gels (SDS-PAGE).

Mouse MAbs were obtained from hybridoma culture supernatant and purified using protein A and subsequent dialysis against PBS. The hCG specific mouse MAbs used was mAB 3299 (anti-Thyroid Stimulating Hormone). The RR-6 specific mouse MAbs used was URL 08-04.

Example I.2

Sub-Saturation Point

Using ELISA, dilution curves were made for all antibodies. From these dilution curves subsaturation point was determined (FIG. 1). The sub-saturation point was defined as the highest concentration on the linear part of the curve. Using this sub-saturation point any effect on antigen binding can be observed as a decrease in signal.

Example I.3

Temperature

Llama $V_{HH}$s and mouse MAbs were incubated at various temperatures (4° C., 60° C., 70° C., 80° C. and 90° C.) for two hours. Subsequently, antibodies were put 30 minutes at 25° C. and stored at 4° C. Samples were diluted to sub saturation point and ELISA was performed (FIG. 2). It can be concluded that the $V_{HH}$ fragments are more stable than the MAbs.

Example I.4

Binding in the Presence of Ammonium Thiocyanate

Double ATC (0-8M) concentrations were mixed 1:1 with double sub saturation concentrations of antibodies and were incubated for 10 min at room temperature. Standard ELISA was performed using antibody-ATC mixtures. See FIG. 3.

From FIGS. 3B and 3D it can be concluded that the llama $V_{HH}$ fragments HI-15 and R7 are able to bind at higher concentrations ammonium thiocyanate than any of the RR-6 or hCG specific mouse MAbs tested. The binding of HI-15 was reduced only 20% in 4M ammonium thiocyanate, whereas none of the other antibodies tested were able to bind at this concentration. Llama $V_{HH}$ fragment R7 was completely inhibited in RR-6 binding at 4M ammonium thiocyanate, whereas the best anti RR-6 Mabs (URL 08-01 and URL 08-13) were already completely inhibited at 2M ammonium thiocyanate (FIG. 3C).

Based on these findings applicants are of the opinion that it is well within the ability of the skilled person to find VHHs which are stable under conditions which are normally destabilising for traditional antibodies such as Mouse Mabs.

Example I.5

Specificity of Llama $V_{HH}$s

ELISA was performed on separate alpha-, beta-subunit, or native hCG. The results are shown in Table 1.

TABLE 1

| Specificity llama $V_{HH}$s anti-hCG | | | |
|---|---|---|---|
| Llama $V_{HH}$ | Alpha | Beta | Intact |
| HI-6 | − | + | + |
| H-13 | + | − | + |
| H-14 | + | − | + |
| HI-15 | + | − | + |
| HI-113 | − | − | + |

Within this small subset, llama $V_{HH}$s were found specific to separate alpha, beta, or native hCG. This indicates that llama $V_{HH}$s have the same potential as mouse MAbs in recognition of antigen.

Example I.6

Affinity

Apparent affinities of a selection of llama $V_{HH}$s were determined by kinetic measurements using the IAsys Biosensor (Affinity Sensors, Cambridge, UK). The results are given in Table 2 below.

TABLE 2

Affinity values llama $V_{HH}$s and mouse MAbs

| Llama $V_{HH}$ | Kd (nM) | Mouse Mab | Kd (nM) |
|---|---|---|---|
| H-14 | 300-400 | URL 08-04 | 1 |
| R2 | 22 | Fab URL 08-04 | 8.4 |
| R7 | 45 | Mab 3299 | 3 |
| R8 | 20 | | |
| R9 | 83 | | |
| R10 | 58 | | |

Example II.1

Induction of Humoral Immune Responses in Llama

A male llama was immunized with K88ac fimbriae, also known as F4 fimbriae, which were purified from *E. coli* strain 1087 according to Van Zijderveld et al. (1990). Immunizations were performed both subcutaneously and intramuscularly using 1 ml 50 mg/l K88ac per immunization site. The first two immunizations were performed with a three week interval and using a water in oil emulsion (4:5 (v/v) antigen in water:specol) as described by Bokhout et al. (1981 and 1986). The third and fourth immunization were done without adjuvant, five and nine weeks after the first immunization. The immune response was followed by antigen specific ELISA's.

Polystyrene microtiter ELISA plates (Greiner HC plates) were activated overnight at 4° C. with 100 µl/well of 5 mg/l K88ac antigen in 0.05 M sodium carbonate buffer at pH 9.5. After each incubation plates were washed four times with 0.05% (v/v) Tween 20 in demi water in order to remove unbound proteins. The wells were then successively incubated 1 hr at ambient temperature with 100 Fl antibody solution in blocking buffer (PBS containing 2% (w/v) BSA; 0.05% (v/v) Tween 20; 1% (v/v) culture supernatant of a *S. cerevisiae* strain, SU 50 (Giuseppin, et al., 1993) grown on YPD; 1% (v/v) of a cleared lysate of *E. coli* JM109 cells). The antigen sensitized plates were then successively incubated with (1) serially diluted llama serum samples, (2) 2000-fold diluted polyclonal rabbit anti llama serum (obtained via immunizing rabbits with llama immunoglobulines which were purified via ProtA and ProtG columns), (3) 2000-fold diluted swine-anti-rabbit immunoglobulins conjugated with horse radish peroxidase. The bound peroxidase activity was determined using the substrate 3,3',5,5'-tetramethylbenzidine.

Example II.2

Cloning, Expressing and Screening of Llama $V_{HH}$ Fragments

II.2.1 Isolation of Gene Fragments Encoding Llama $V_{HH}$ Domains.

From an immunized llama in accordance to Example II a blood sample of about 200 ml was taken and an enriched lymphocyte population was obtained via Ficoll (Pharmacia) discontinuous gradient centrifugation. From these cells, total RNA was isolated by acid guanidium thiocyanate extraction (e.g. via the method described by Chomczynnski and Sacchi (1987). After first strand cDNA synthesis (e.g. with the Amersham first strand cDNA kit), DNA fragments encoding $V_{HH}$ fragments and part of the long or short hinge region where amplified by PCR using specific primers:

```
                                           (see SEQ. ID. NO: 1)
                 PstI
V_H - 2B 5'-AGGTSMARCTGCAGSAGTCWGG-3'
S = C and G, M = A and C, R = A and G, W = A and T, (see SEQ. ID. NO: 2)
              HindIII
Lam-075'-AACAGTTAAGCTTCCGCTTGCGGCCGCGGAGCTGGGGTCTTCGCTGTGGTGCG-3'
(short hinge)

(see SEQ. ID. NO: 3)
              HindIII
Lam-085'-AACAGTTAAGCTTCCGCTTGCGGCCGCTGGTTGTGGTTTTGGTGTCTTGGGTT-3'
(long hinge)
```

Upon digestion of the PCR fragments with PstI (coinciding with codon 4 and 5 of the $V_{HH}$ domain, encoding the amino acids L-Q) and BstEII (located at the 3'-end of the $V_{HH}$ gene fragments, outside and upstream of the 08 primer coinciding with the amino acid sequence Q-V-T), the DNA fragments with a length between 300 and 450 bp (encoding the $V_{HH}$ domain, but lacking the first three and the last three codons) were purified via gel electrophoresis and isolation from the agarose gel.

II.2.2 Construction of *Saccharomyces cerevisiae* Expression Plasmids Encoding Llama $V_{HH}$ Domains Plasmids pUR4547 (CBS 100012) and pUR4548 (CBS 100013) are *Saccharomyces cerevisiae* episomal expression plasmids, derived from pSY1 (Harmsen et al., 1993). Both plasmids contain the GAL7 promoter and PGK terminator sequences as well as the invertase (SUC2) signal sequence. In both plasmids the DNA sequence encoding the SUC2 signal sequence is followed by the first 5 codons (encoding Q-V-Q-L-Q; see SEQ. ID. NO: 4) of the $V_{HH}$ domain (including the BstII site), a stuffer sequence, the last six codons (encoding Q-V-T-V-S-S; see SEQ. ID. NO: 5) of the $V_{HH}$ domain. In pUR4547, this is followed by two stop codons, an AflII and HindIII site. In pUR4548, the Q-V-T-V-S-S (SEQ. ID. No: 5) sequence is followed by eleven codons encoding the myc-tag, two stop codons, an AflII and HindIII site.

Plasmids pUR4547 and pUR4548 were deposited under the Budapest Treaty at the Centraal Bureau voor Schimmelcultures, Baarn (The Netherlands) on 18 Aug. 1997 with deposition numbers CBS 100012 and CBS 100013, respectively. In accordance with Rule 28(4) EPC, or a similar arrangement from a state not being a contracting state of the EPC, it is hereby requested that a sample of such deposit, when requested, will be submitted to an expert only.

Upon digesting pUR4548 with PstI and BstEII, the about 6.4 kb vector fragment was isolated and ligated with the PstI-BstEII fragments of between 300 and 450 bp obtained as described above. After transformation of *S. cerevisiae* via electroporation, transformants were selected from minimal medium agar plates (comprising 0.7% yeast nitrogen base, 2% glucose and 2% agar, supplemented with the essential amino acids and bases).

II.2.3 Screening for Antigen Specific $V_{HH}$ Domains

For the production of llama $V_{HH}$ fragments with myc-tail, individual transformants were grown overnight in selective minimal medium (comprising 0.7% yeast nitrogen base, 2% glucose, supplemented with the essential amino acids and bases) and subsequently diluted ten times in YPGal medium (comprising 1% yeast extract, 2% bacto pepton and 5% galactose). After 24 and 48 hours of growth, the culture supernatant of the colonies was analysed by ELISA for the presence of $V_{HH}$ fragments which specifically bind to the *E. coli* K88 antigen, in essential the same way as described in Example 1. In this case, however, the presence of specifically bound $V_{HH}$ fragments was detected by incubation with monoclonal anti-myc antibodies, followed by incubation with polyclonal rabbit-anti-mouse conjugate with alkaline phosphatase.

In this way a number of $V_{HH}$ fragments have been obtained, which specifically recognise the *E. coli* K88 antigen.

Two examples of such fragments are given below:

K607

(see SEQ. ID. NO: 6)
QVQLQESGGG LVQPGGSLRL SCAASGGTFS ASAMTWYRQA PGKSREYVAR IFFSGGTNYA

DSVKGRFTIS RDNAKNTMYL QMNDLKREDT AVYYCNLLSY WGQGTQVTVS S

K609

(see SEQ. ID. NO: 7)
QVQLQESGGG LVQPGGSLRL SCAASGGTFS WYAMGWFRQA PGKEREFVAT VSRGGGSTYY

ADSVKGRFTI SRDNAKNTVY LQMNSLKPED TAAYYCAAGR GSPSDTGRPD EYDYWGQGTQ

VTVSS

Example II.3

Construction of "Self-Cloning" Yeast Expression Cassette, Encoding a Chimeric Protein Anchored to the Cell Wall of Yeast, Comprising a Binding Domain and a Cell Wall Anchor In order to display a binding domain at the yeast cell wall, a genetic fusion of the gene encoding the binding domain and a gene encoding the cell wall anchor has to be constructed, either with or with out a linker sequence, essentially as described in WO 94/25591. As an example, the construction of a "self cloned" yeast, displaying a llama $V_{HH}$ fragment fused via the "long hinge" region to the a-agglutinin cell wall anchor will be described below. Obviously this can be done in much the same way for different binding domains, different linkers/hinges and different cell wall anchors.

II.3.1 Isolation of the Llama "Heavy Chain" Long Hinge Sequence.

For the isolation of the hinge regions of the llama "heavy chain" antibodies, the cDNA which was obtained as described in Example 1, was amplified by PCR using the primers $V_H$-2B and Lam-03. The nucleotide sequence of the latter primer was based on a consensus sequence based on the $C_H2$ domains of different species. The PCR reaction resulted in three DNA fragments of about 450 (a), 550 (b) and 850 (c) bp.

(see SEQ. ID. NO: 8)
BamHI
Lam-03 GGTATGGATCCACRTCCACCACCACRCAYGTGACCT

Upon digesting these fragments with PstI and BamHI and size fractionation, they were ligated into pEMBL (Dente, 1983) and subjected to nucleotide sequence analysis. The clones obtained from the DNA fragment with an average length of ~450 bp (a) were found to comprise a short hinge region, having the following sequence:

```
                                                         (see SEQ. ID. NO: 9 and 29)
         V_HH     ><             short hinge                       >
GGTCACCGTCTCCTCAGCGCACCACAGCGAAGACCCCAGCTCCAAGTGTCCCAAATGCCCA
 V  T  V  S  S  A  H  H  S  E  D  P  S  S  K  C  P  K  C  P
                  <-       LAM 07 WB            <-1
```

The clones obtained from the DNA fragment with an average length of ~550 bp (b) was found to comprise a long hinge region, having the following sequence:

```
                                                    (see SEQ. ID. NO: 10 and 30)
 BstEII    V_HH    ><                                       long hinge
GGTCACCGTCTCCTCAGAACCCAAGACACCAAAACCACAACCACAACCCACAACCACAACCCAAT
 V  T  V  S  S  E  P  K  T  P  K  P  Q  P  Q  P  Q  P  Q  P  N
                <-         LAM 08 WB          <-1

>
CCTACAAYAGAATCCAAGTGTCCCAAGTGTCCA
 P  T  T  E  S  K  C  P  K  C  P
```

For the construction of pUR4588 (FIG. 5), a NheI site was introduced in the 3'-end of the long hinge region via PCR using the primers:

```
                                           (see SEQ. ID. NO: 11)
           NheI
BOLI 18 CGCGGCTAGCCTTGGATTCTGTTGTAGGATTGGGTTG (see SEQ. ID. NO: 12)
        BstEII
LH    CCCAGGTCACCGTCTCCTCAGAACCCAAG via which the following sequence:
                                 (see SEQ. ID. NO: 13 and 31)
CCTACAACAGAATCCAAGTGTCCCAAGTGTCCA
 P  T  T  E  S  K  C  P  K  C  P
``` became

```
                                 (see SEQ. ID. NO: 14 and 32)
                     II
         CCTACAACAGAATCCAAGGCTAGC
          P  T  T  E  S  K  A  S
```

Upon digestion with BstEII and NheI, an about 90 bp fragment was obtained encoding the last 4 amino acids of the V_HH domain and the long hinge region except for the last 5 amino acids.

II.3.2 Adaptation of the α-Agglutinin Gene

Plasmid pUR4482 (FIG. 4) is a yeast episomal expression plasmid for expression of a fusion protein with the invertase signal sequence, the CH_F09 variable region, the Myc-tail and the Camel "X-P-X-P" Hinge region (see Hamers-Casterman et al., 1993), and the α-agglutinin cell wall anchor region.

The PstI-site at position 1665 in the α-agglutinin gene was removed via a three step PCR using primers PAF01 to PAF04. For easy cloning and sequencing in pEMBL8, EcoRI and HindIII sites were introduced at the 3'- and 5'-end of the gene fragment encoding α-agglutinin, respectively. PCR-A using primers PAF01 and PAF02 on a pUR4482 template resulted in an about 707 bp fragment with the EcoRI restriction site at the 3'-end. PCR-B using primers PAF03 and PAF04 on a pUR4482 template resulted in an about 427 bp fragment with the HindIII site at the 5'-end. A third PCR was performed with the fragments obtained from reaction A and B, together with the primers PAF01 and PAF04. After digesting the obtained PCR product (~1135 bp), which comprises the modified α-agglutinin gene without the PstI restriction site, with EcoRI and HindIII, the resulting ~1130 bp fragment was ligated into the vector fragment of pEMBL8 which was digested with the same enzymes resulting in pRL03.

```
PCR-A
                                           (see SEQ. ID. NO: 15)
    PAF01 GGAATTCGTCTCCTCAGAACAAAAAC (see SEQ. ID. NO: 16)
    PAF02 GCTGCTGCAAAAGGAATTTA 5 PCR-B
                                           (see SEQ. ID. NO: 17)
    PAF03 AAATTCCTTTTGCAGCAGC (see SEQ. ID. NO: 18)
    PAF04 GGGAAGCTTCGACAAAAGCAGAAAAATGA
```

In essentially the same way as for the removal of the PstI site, the SapI site in the α-agglutinin coding sequence at position 1618 was removed from plasmid pRL03. PAF01 and BOLI-20 were used in a PCR reaction with pRL03 as template to generate an approximately 660 bp fragment and primers BOLI19 and PAF04 were used to make an approximately 504 bp fragment which were linked by splicing by overlap extension using primers PAF01 and PAF04 (PCR-C).

```
    PCR-A
                                           (see SEQ. ID. NO: 19)
    PAF01 see above
    BOLI-20 TTACAAAAGTGGGTTCTTCAGATGGAA PCR-B
                                           (see SEQ. ID. NO: 20)
    BOLI-19 TTCCATCTGAAGAACCCACTTTTGTAA
    PAF04 see above
```

PCR-C
Product of PCR-A and PCR-B and PAF01 and PAF04.

Again an about 1130 bp EcoRI-HindIII fragment was obtained and cloned in pEMBL8.

Finally, the SacI site at position 2041 can be removed and a HindIII site can be introduced downstream of the stop codon by replacing the sequence:

```
                                 (see SEQ. ID. NO: 33 and 34)
    SacI                                      HindIII
    gagctCGGTTCGATCATTTTTCTGCTTTTGTCGAagctt cTCGAGCCAAGCTAGTAAAAAGACGAAAACAGCTTCGAa
     E  L  G  S  I  I  F  L  L  L  S
``` with a synthetic linker having the sequence:

(SacI)                                                              (see SEQ. ID. NO: 21 and 35)
                                                                                      HindIII
gagctGGGTTCGATCATTTTTCTGCTTTTGTCGTACCTGCTATTCTAAGATCTGATTAAACGCGTGAagctt cTCGACCCAAGCTAGTAAAAAGACGAAAACAGCATGGACGATAAGATTCTAGACTAATTTGCGCACTTCGAa
 E  L  G  S  I  I  F  L  L  L  S  Y  L  L  F  *

In this way a plasmid was obtained containing an about 990 bp NheI-HindIII fragment encoding the C-terminal 320 amino acids of the α-agglutinin in which the PstI, SapI and SacI sites were removed via silent mutations in order to facilitate further construction work.

II.3.3 Construction of pUR4588

The following fragments were subsequently joined:

i) the about 100 bp SacI-PstI fragment of pUR4548: comprising a part of the Gall promoter, the SUC2 nucleotide sequence and the first 4 codons of the $V_{HH}$ fragment, ii) the about 350 bp PstI-BstEII fragment, which was obtained as described in Example 2: encoding a truncated $V_{HH}$ fragment, missing both the first 4 (QVQL; see SEQ. ID. NO: 4) and the last 5 (VTVSS; see SEQ. ID. NO: 5) amino acids of the $V_{HH}$ fragment, iii) the about 90 bp BstEII-NheI fragment obtained as described in Example 3.1: encoding the last 5 amino acids of the $V_{HH}$ fragment and the long hinge region, and iv) the about 1 kb NheI-HindIII fragment obtained as described in 3.2: the adapted α-agglutinin gene.

Figure 7:
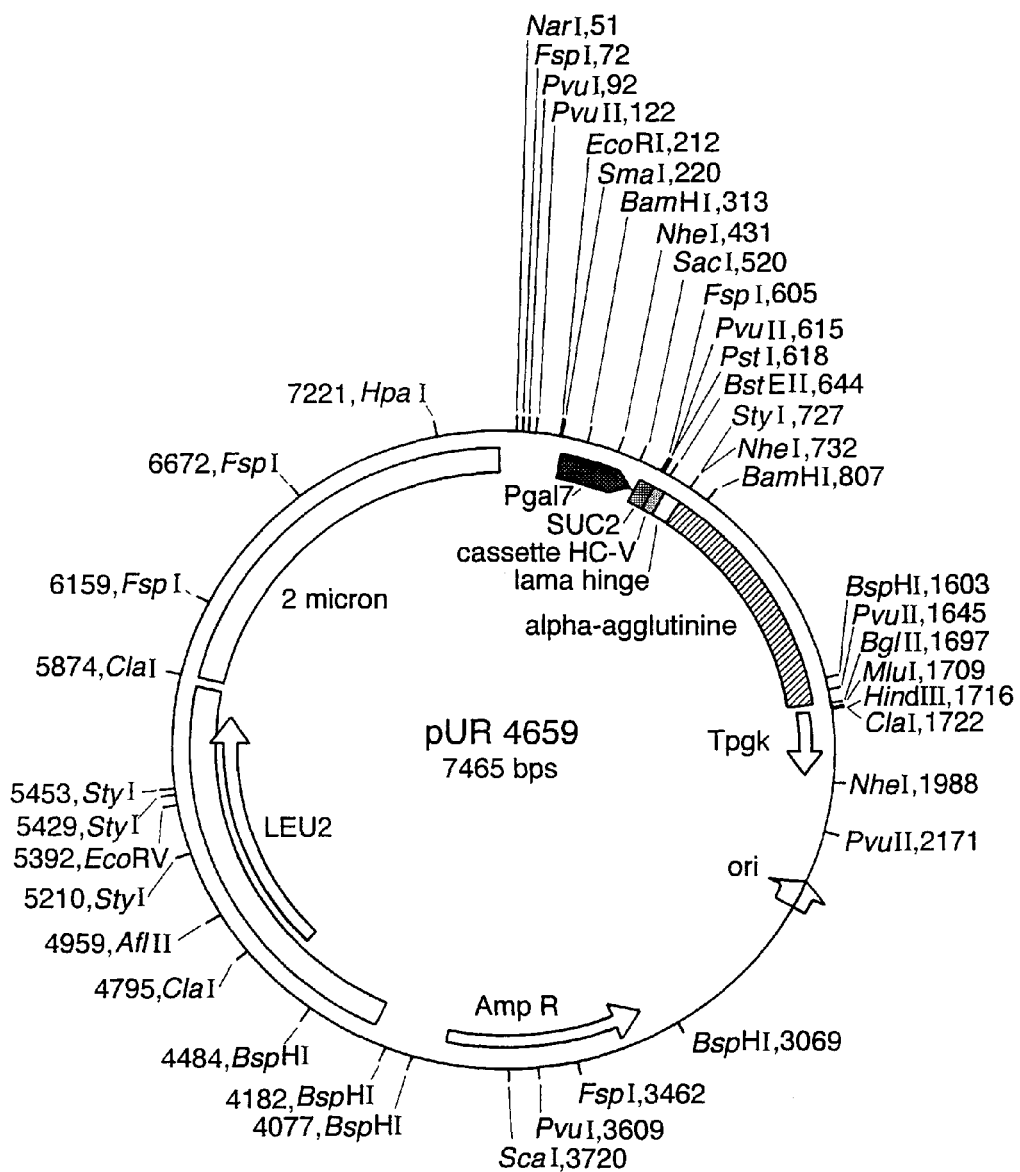
FIG. 7 represents a restriction map of plasmid pUR 4659

Finally, the thus obtained about 1.5 kb SacI-HindIII fragment was ligated into the about 7.5 kb vector fragment of pUR2822 which was digested with the same enzymes, resulting in pUR4588 (FIG. 7).

Plasmid pUR2822 was deposited under the Budapest Treaty at the Centraal Bureau voor Schimmelcultures, Baarn (The Netherlands) on 29 Sep. 1998 with deposition number CBS 101292. In accordance with Rule 28(4) EPC, or a similar arrangement from a state not being a contracting state of the EPC, it is hereby requested that a sample of such deposit, when requested, will be submitted to an expert only.

II.3.4 Production of Yeast Strains "Functionally" Expressing the Chimeric Protein Plasmid pUR4588 (FIG. 5) was digested with SapI, after which an about 6.7 kb fragment was purified, via gel electrophoresis and isolated from the agarose gel. This fragment was introduced into yeast strains via electroporation. Transformants containing (multicopies of) the DNA fragment integrated into the rDNA locus of their genome were selected as described in Example 2. Induction of the production and display of the binding domain was also done as described in Example 2. In order to determine the functionality of the binding domains displayed at the yeast cell wall, the following assay was performed:

The yeast cells were diluted in PBS containing 0.05% (v/v) Tween 20 (PBST) to an $A_{660}$=1 and 10 µl of this suspension was mixed with 1 µg K88ac antigen in 100 µl PBST in an Eppendorf tube and incubated for 1 hr at ambient temperature. Unbound antigen was removed from the yeast cells by three washes in 1 ml PBST. Cells were collected after each wash by centrifugation and aspiration of the supernatant. The yeast cells were subsequently resuspended in 100 µl of PBST containing a conjugate of monoclonal antibody AD11, which is specific for K88, and horse radish peroxidase (AD11-HRPO; Van Zijderveld et al., 1990). After 1 hr incubation at ambient temperature the cells were washed again three times with PBST. The amount of AD11-HRPO bound to the yeast cells was taken as a measure of the amount of functional K88-binding domains displayed at the yeast cell wall. This value was determined by performing a peroxidase assay on serial twofold dilutions of these cells, using 3,3',5,5'-tetramethylbenzidine as a substrate, and measuring the $A_{450}$. The recovered functionality (RF) of the displayed antibody fragments after a physical treatment to inactivate the S. cerevisae cells is defined as the $A_{450}$ before treatment (is F0) divided by the $A_{450}$ after treatment (is Ft).

Example III

Heat Inactivation of $V_{HH}$s

III.1 Production of Biomass Suspension.

Saccharomyces cerevisiae strain SU50 containing the genomically integrated expression plasmid pUR4588 (FIG. 5) was used. The strain was grown in a 10 l scale fermentor using a fed batch fermentation set up (Mendoza-Vega et al., 1994). Such a fermentation consists of two steps: the first step (the batch phase) is performed in a Yeast extract and Peptone (YP) medium containing glucose. In the second step (the feed phase) YP medium is added containing glucose and galactose, in order to induce the promoter for the production of the $V_{HH}$-agglutinine fusion. In this way a culture was obtained with a cell density of about $10^9$-$10^{10}$ per ml, comparable to large scale fermentations.

Cell density or viable counts (N) were determined by making decimal dilutions of a cell culture in sterile pepton physiological salt (PFS; 0.85% NaCl, 0.1% Bactopepton (Difco), pH 7). Samples of these dilutions were plated on YPD agar and incubated for 5 days at 30° C. after which the number of colonies were counted. The reduction of viable counts (RVC) after treatment to inactivate the S. cerevisiae cells is defined as the logarithm of the viable counts after treatment (is Nt) divided by the number of viable counts before treatment (is N0); Log(Nt/N0).

III.2 Heat Treatment

Determination of the killing efficiency of heat treatment on high cell density cultures was performed using one of two different approaches, as desired.

III.2.1 Using Glass Capillaries

Sterile glass capillaries (Fisher Scientific Den Bosch, l=100 mm, d=2 mm) were filled with 0.1 ml of the yeast culture medium and sealed. After incubating the filled, sealed capillaries, they were placed for a set time in a water bath at the desired temperature (experiments were performed at quadruplets). After this the recovered functionality (RF) and the reduction in viable counts (RVC) for the different samples was determined as described above.

III.2.2 Using aluminium vials

Sterile aluminium cryo vials (Omnilabo, volume 3 ml) were filled with 0.5 ml of the yeast culture for each temperature/time combination (experiments performed in duplo). The vials were placed in a water bath at the desired temperature and time. After this the recovered functionality (RF) and the reduction in viable counts (RVC) for the different samples was determined as described above.

III.3 Viable Counts and GI-ELISA

From the yeast culture the viable counts (N0) and the GI-ELISA signal (F0) was determined before heat treatment.

The same was done for the samples obtained as described above (Nt and Ft, respectively). The results are presented in Table 3 below.

TABLE 3

| Temp (° C.) | time (sec) | RVC (=log (Nt/N0)) | RF (=Ft/F0) |
|---|---|---|---|
| 60 | 300 | −4 | 100% |
| 62 | 60 | >−6 | 100% |
| 70 | 30 | >−7 | >85% |
| 74 | 15 | >−7 | >85% |

Example IV

Inactivation of S. cerevisiae SU50 (pUR 4588) with Ultra High Pressure

From literature it is known that at pressures over 300 MPa proteins FF ATP-ase can be inactivated (Wouters et al, 1998).

S. cerevisiae SU50 (pUR4588), displaying anti-E. coli K88 $V_{HH}$ fragments, was grown at 10 liter scale as described above. Samples of 1.5 ml were taken and transferred to bags for Ultra High Pressure treatment in a "Food Lab Multi Vessel" (Stansted Fluid Power, UK). Samples were incubated at three different pressures 250, 300 and 325 Mpa for different periods of time. The survival of the yeast cells and the functionality of the displayed $V_{HH}$s was determined as described above. The results are presented in Table 4 below.

TABLE 4

| Pressure (Mpa) | time (min) | RVC (=log (Nt/N0)) | RF (=Ft/F0) |
|---|---|---|---|
| 250 | 60 | −9 | 100% |
| 300 | 3 | −6 | >70% |
|  | 20 | −9 | >70% |
| 325 | 1 | −6 | 70% |
|  | 3 | −9 | 70% |
|  | 20 | −9 | 70% |

It was further found that yeast cells that do not have the capacity to synthesize trehalose are much more sensitive for UHP (Fernandes et al., 1997). Therefore, a preferred embodiment of the inactivation of yeast with UHP is, instead of using a wild type yeast strain, using a variant strain defective in the synthesis of trehalose, e.g. a strain in which the TPS1 gene has been inactivated e.g. by partial or complete deletion. In this way the UHP treatment could be reduced from 300 MPa to 200 MPa with the same reduction in viable counts.

Example V

Killing of Yeast Cells by Irradiation

An alternative for inactivation of yeast cells is gamma irradiation. S. cerevisiae SU50 (pUR4588), was grown at 10 liter scale as described above. After fermentation the biomass slurry was transferred to polypropylene drums and exposed to 10 kGray or 25 kGray of gamma irradiation (GAMMASTAR, Ede). The survival of the yeast cells and the functionality of the displayed $V_{HH}$s was determined as described above. For both cases, the RVC was better than—10 (no viable counts left after irradiation), whereas the RF of the $V_{HH}$s was 100%. The anti-K88 activity was not affected by the irradiation.

A number of genes involved in DNA repair are known (e.g rad9, rad30, rad52, sir2, sir3, sir4). Yeast strains carrying mutations in these genes, are known to be more sensitive towards radiation (Friedberg et al., 1991; Tsukamoto et al., 1997). In a preferred embodiment of this invention, a yeast strain with one or more mutations in one or more of these genes is used.

Example VI

Combined Effect of Heat Inactivation and Antimicrobials on Saccharomyces cerevisiae S. cerevisiae SU50 (pUR4588) cells were cultivated and harvested as described above and subjected to heat treatment as described above in the presence of antimicrobials like ethanol, potassium sorbate and antimicrobial peptides like nisin and MB21. According to the methods described in the previous examples the inactivation efficiency and the recovery of the functionality of the $V_{HH}$ antibodies have been determined. The results are given in Table 5 below.

TABLE 5

Inactivation of S. cerevisiae and $V_{HH}$ as function of the temperature and the concentration of antimicrobials

| Temp (° C.) | Antimicrobials | Time (min) | RVC (=log Nt/No) | RF (=Ft/Fo) |
|---|---|---|---|---|
| 50 | 3% ethanol | 60 | 0 | 100% |
| 50 | 0.2% K-sorbate | 60 | 0 | 100% |
| 60 | — | 5 | −4 | 100% |
| 60 | 3% ethanol | 5 | −7 | 90% |
| 60 | 0.2% K-sorbate | 5 | −8 | 95% |

It has been reported that yeast cells that do not have the full capacity of synthesising multi drug resistant proteins are much more sensitive to weak acids, e.g. sorbic acid (PDR12; Piper et al., 1998). Therefore, a preferred embodiment of inactivation of yeast by a combination of heat and acid is to use, instead of the wild type yeast strain, a strain in which the PMR gene is inactivated, e.g. via partial or complete deletion. In this way either the temperature or the amount of acid or both can be reduced considerably.

Example VII

Animal Feeding Trials with Yeast Displaying Anti E. Coli K88 $V_{HH}$s on their Surface In this experiment two groups of piglets were used. A mild E. coli K88 infection was induced in all animals by an oral dose of $10^6$ E. coli K88 cells. For group I (exp. group) the feed was supplemented with 6 ml of a concentrated suspension ($10^{10}$-$10^{11}$ cells per ml) of SU50 (pUR4588), and for group II (control) with the same amount of wild type SU50 yeast. The yeast cells were inactivated with gamma irradiation according to the procedure as described in Example 6.

Number of affected piglets due to dosing of >10⁶ *E. coli* K88/g in the meal.
See Table 6 below.

TABLE 6

| Day | Control | Exp group |
|---|---|---|
| 0 | 0 | 0 |
| 1 | 22 | 17 |
| 2 | 50 | 19 |

Conclusion: protective effect clearly visible after 2 days.

Example VIII

Dye Transfer Prevention Using HCV Antibodies

Cotton swatches dyed with RR6 were prepared by soaking pieces of cotton (5*5 cm) in a solution of RR6 for 30 min (0.1 M borate buffer, pH 8.5, 0.15 M NaCl). After drying, these swatches were washed in the presence of various concentrations of a VHH (R7 anti-RR6 as disclosed in example 1). For the monitoring of dye transfer, a white cotton swatch (dye pick-up swatch) was added. As wash solution, a carbonate buffer (pH 9) was used, to which in a number of experiments surfactants were added. These were alkyl benzene sulfonate (LAS, 600 mg/l), and a LAS/Synperonic A7 mixture (290 mg/l LAS, 660 mg/l SA7).

After the wash the swatches were line dried and the reflectance spectra were measured using a Minolta spectrometer. The data thereby obtained were transferred to the CIELAB L*a*b* colour space parameters. In this colour space, L* indicates lightness and a* and b* are the chromaticity coordinates. The colour differences between the swatches prior to washing and after the wash, were expressed as ΔE indicating the distance in the colour space between before and after washing.

The results, given as the ΔL, Δa, Δb, and ΔE of the dye pick-up swatches after the experiment, with respect to white cotton are given in the table below.

TABLE 7

| Conditions applied | ΔL | Δa | Δb | ΔE |
|---|---|---|---|---|
| Buffer, pH 7 containing VHH against RR6 at concentration: | | | | |
| 0 μM | 2.9 | −5.7 | 2.2 | 6.8 |
| 1.25 μM | 1.9 | −4.1 | 1.7 | 4.9 |
| 2.5 μM | 2.0 | −4.3 | 1.9 | 5.2 |
| 5.0 μM | 0.6 | −1.4 | 0.8 | 1.8 |
| 10.0 μM | 0.6 | −1.1 | 0.6 | 1.4 |
| Buffer, pH 9 containing VHH against RR6 at concentration: | | | | |
| 0 μM | 3.3 | −5.4 | 2.1 | 6.7 |
| 1.25 μM | 2.1 | −4.8 | 2.0 | 5.7 |
| 2.5 μM | 1.6 | −3.5 | 1.5 | 4.2 |
| 5.0 μM | 0.7 | −1.7 | 0.8 | 2.1 |
| 10.0 μm | 0.1 | −0.5 | 0.4 | 0.7 |
| LAS solution, pH 9, containing VHH against RR6 at concentration: | | | | |
| 0 μM | 2.0 | −4.3 | 1.9 | 5.1 |
| 10.0 μM | 1.1 | −2.6 | 1.2 | 3.1 |
| LAS/SA7 solution, pH 9, containing VHH against RR6 at concentration: | | | | |
| 0 μM | 2.0 | −4.2 | 1.8 | 5.0 |
| 10.0 μM | 0.1 | −0.2 | 0.1 | 0.3 |

These results illustrate that anti-RR6 antibodies are able to prevent dye transfer, especially at levels of above 2.5 μM during use and that these VHHs remain stable in the presence of surfactants especially mixed surfactants and can hence continue to be effective during the use of laundry detergents.

Example IX

Induction of a Humoral Immune Response in Llama

A male llama was immunised with an oil emulsion (1:9 V/V, antigen in PBS: Specol (Bokhout et al.) subcutaneously and intramuscularly. Per site about 0.75-1.5 ml emulsion was injected containing about 100 μg of a conjugate consisting of the azo-dye RR120 (Cibacron Red 4G-E, Ciba Geigy) which was coupled to BSA via its reactive triazine group.

Immunisations were performed according to the following time schedule: the second immunisation was performed three weeks after the first injection, and the third immunisation two weeks after the second one. The immune response against RR120 was followed by titration of serum samples in ELISA by using Nunc Covalink plates, which where coated with the azo-dye-RR120 (100 μl/well of 2.5 mM RR120 in coating buffer (0.1 M di-sodium tetraborate decahydrate, 0.15 M NaCl pH 8.5), incubation overnight at 50° C.)

After incubation with serum, the bound llama antibodies were detected with poly-clonal rabbit-anti-llama antiserum (obtained via immunising rabbits with llama immunoglobulines purified via ProtA and ProtG columns; ID-DLO) and, as a second step, swine-anti-rabbit immunoglobulines (Dako) conjugated with alkaline phosphatase were used after which the alkaline phosphatase enzyme-activity was determined upon incubation with p-nitro-phenyl phosphate and the optical density was measured at 405 nm.

Example IX.2

Cloning, Selection and Screening of Llama $V_{HH}$ Fragments

IX.2.1 Isolation of Gene Fragments Encoding Llama VHH Domains.

From an immunised llama a blood sample of about 200 ml was taken and an enriched lymphocyte population was obtained via centrifugation on a Ficoll (Pharmacia) discontinuous gradient. From these cells, total RNA was isolated by acid guanidium thiocyanate extraction (e.g. via the method described by Chomczynnski and Sacchi, 1987). After first strand cDNA synthesis using MMLV-RT (Gibco-BRL) and random oligonucleotide primers (Pharmacia), or by using the Amersham first strand cDNA kit, DNA fragments encoding $V_{HH}$ fragments and part of the long or short hinge region were amplified by PCR using specific primers of SEQ ID 1, SEQ ID 2 and SEQ ID 3 as described above.

IX.2.2 Construction and Screening of *S. Cerevisiae* Libraries which Secrete VHH Domains in the Culture Medium.

The DNA-fragments generated by PCR were digested with PstI (coinciding with codon 4 and 5 of the $V_{HH}$ domain, encoding the amino acids L-Q) and BstEII (naturally occurring in FR4 region of the majority of the $V_{HH}$-genes and coinciding with the amino acid sequence Q-V-T). The digested PCR-products, with a length between 300 and 400 bp (encoding the complete $V_{HH}$ domain, but lacking the first and the last three codons), were separated by electrophoresis on agarosegel and, after purification from the gel-slices with the Qiaex-II extraction kit, cloned in the *Saccharomyces cerevisiae* episomal expression plasmids pUR4547 or pUR4548

RR120 specific $V_{HH}$ fragments were isolated via screening of culture supernatants from individual clones in ELISA using either rabbit anti-llama $V_{HH}$ poly-clonal antibody followed by incubation with goat anti-rabbit poly-clonal antibodies conjugated to horse radish peroxidase (Bio-rad) (for $V_{HH}$ fragments cloned in pUR4547); or mouse anti-myc mono-clonal antibody 9E10 followed by incubation with poly-clonal goat-anti-mouse conjugate with horse radish peroxidase (for $V_{HH}$ genes cloned in pUR4548) for detection.

For the production of llama $V_{HH}$ fragments in *S. cerevisiae*, individual transformants were grown overnight in selective minimal medium (comprising 0.7% yeast nitrogen base, 2% glucose, supplemented with the essential amino acids and bases) and subsequently diluted ten times in YPGal medium (comprising 1% yeast extract, 2% bacto pepton and 5% galactose). After 24 and 48 hours of growth, the culture supernatant of the colonies was analysed by ELISA for the presence of antigen specific $V_{HH}$ fragments.

Individual *S. cerevisiae* clones were grown on YPgal for 48 hours in wells of microtiter plates. During the second part of this incubation, fusion protein consisting of a $V_{HH}$ fragment and α-agglutinin is secreted in the growth-medium. Culture supernatants containing these chimeric molecules were tested in ELISA for binding to RR120 using the myc-TAG for detection as described above. For further analysis of selected clones, $V_{HH}$-encoding DNA fragments from these yeast display vectors were recloned in the episomal yeast secretion vector pUR4548 and analysed as described in paragraph 2.2.

IX. 2.4 Construction and Screening of a Phage Library Displaying VHH Domains

Figure 6:
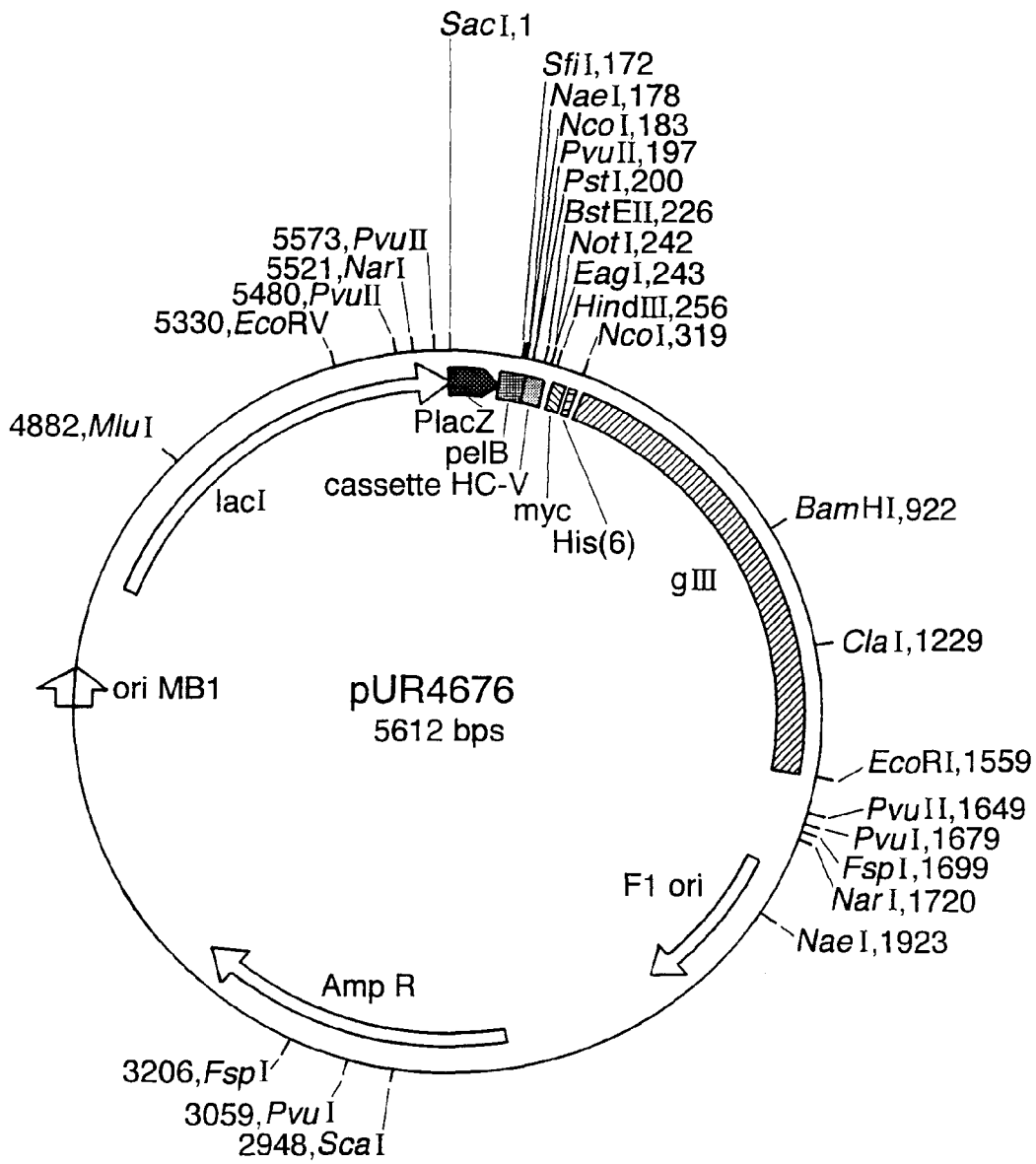
FIG. 6 represents a restriction map of plasmid pUR 4676

FIG. 6 gives a schematic representation of the phagemid vector pUR4676 which was assembled from:

the about 2.85 kbp NcoI/ScaI fragment of pFab5c (Ørum et al., 1993). The BstEII site present in the lacI gene was removed via a silent mutation using PCR mutagenesis.

the about 2.7 kbp NcoI/ScaI fragment of pHEN1 (Hoogeboom et al., 1991).

The DNA fragment between the PstI site and the first codons of geneIII were replaced with the following sequence (SEQ ID NO: 22):

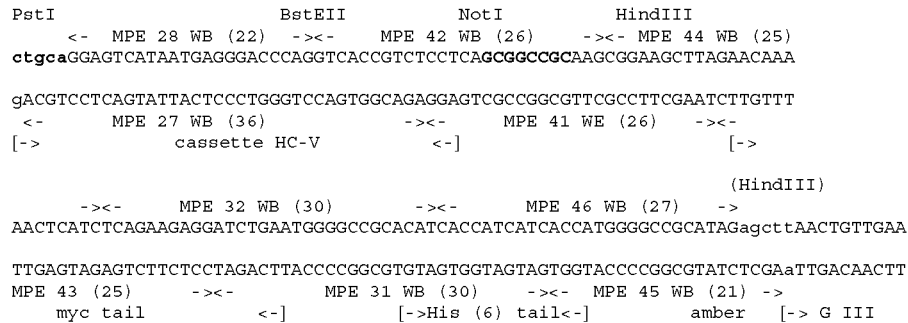

IX.2.3 Construction and Screening of *S. Cerevisiae* Libraries which Display VHH Domains at the Cell Surface.

The PCR-products obtained as described in IX.2.1 can be digested with PstI and BstEII and cloned in the yeast display vector pUR4659 (FIG. 7) as gene-fragments encoding the $V_{HH}$-domain including the hinge region. In this way $V_{HH}$ antibody domains were displayed on yeast cell surface by means of N-terminal fusions onto the cell wall protein α-agglutinin (see patent WO 94/01567). Such a yeast display library with $1 \times 10^6$ clones was constructed in the episomal yeast expression vector pUR4659. Transformed yeast cells were pooled and grown for about 17 hours on selective minimal medium until the $OD_{660}$ was 2. Subsequently, these cells were inoculated into YPGal for expression, secretion and display of the $V_{HH}$ antibody fragments on the cell surface and grown for appr. 17 hours. Secreted $V_{HH}$-fragments were removed by washing the cells with PBS, thereby avoiding a disturbing competition for binding to antigen between yeast bound and free $V_{HH}$ domains.

For the isolation of RR120 binding VHH fragments, the VHH displaying *S. cerevisiae* cells were incubated for two hours with in vitro biotinylated BSA-RR120 in PBS followed by an incubation with FITC-labelled streptavidin. Fluorescence of individual yeast cells was analysed by means of a FACS (Fluorescence Activated Cell Sorter) and the cells with give above average fluorescent signals were selected and inoculated in minimal medium for a second round selection. In this second round, cells with the highest fluorescent signals were selected and propagated as single colonies for analysis or grown for further rounds of selections.

resulting in pUR4676.

Upon digesting this vector with PstI and HindIII and subsequent ligation in the presence of the PCR fragments produced as described in 2.1 and digested with PstI/HindIII, the VHH phagemid libraries were obtained.

IX.2.2.1. Selection of the VHH Library.

From the phagemid libraries, VHH displaying phage particles were produced via superinfection with phage M13-K07 (Promega) essentially as described by (Marks et al., 1991). Selection of the VHH phage library was performed essentially as described by (Marks et al., 1991) via three rounds of panning using RR120 coated immunotubes. The immunotubes (Nunc; Maxisorp, 75×12 mm) were coated with 4 ml 2.5 mM RR120 in coating buffer (0.1 M di-sodium tetraborate decahydrate and 0.15 M NaCl pH 8.5) overnight at 50° C. After blocking with Marvel (2% in PBS) and washing with PBS, about 10E12 phages (preincubated in 4 ml 2% Marvel in PBS for 15 minutes) were added to the tubes. Upon incubation for 1 hour (on turntable) the tubes were washed 15 times with PBST (PBS with 0.1% tween) and 2 times with PBS. Bound phages were subsequently eluted by adding 2 ml 100 mM triethylamine.

The eluted phages were added to 1 M Tris pH 7.4 for neutralisation before adding *E. coli* cells for infection/phage rescue. This process was repeated three times.

Subsequently, single *E. coli* colonies were transferred to microtiter plates and grown overnight in 150 microliter 2×TY medium containing ampicillin (100 microgram per ml) and IPTG (0.8 mM). The culture supernatant was subsequently tested in an antigen specific ELISA.

In this way a large number of RR120 binding VHH domains could be isolated.

For further analysis of selected clones, $V_{HH}$-encoding DNA fragments from these phage display vectors can be recloned in the episomal yeast secretion vector pUR4548 and analysed as described in paragraph IX.2.2.

IX.3 Selection of RR120 Recognising $V_{HH}$ Domains Via Yeast Display in Consumer Products Under Application Conditions.

To enrich for VHH fragments stable in product formulations the screening as described in 2.3 was repeated using application conditions.

In this example we have dissolved the yeast cells in commercially available detergent formulations resp 6 g/l Dutch Omo® (without protease, hereafter referred to as Omo) followed by the addition of the biotinylated BSA-RR120. After a one hour incubation under application conditions, unbound RR120 and detergent were discarded by centrifugation. Subsequently, the cells were incubated with FITC-labelled streptavidin and analysed as described above.

IX.4 Selection of RR120 Recognising $V_{HH}$ Domains Via Phage Display in Consumer Products Under Application Conditions.

IX.4.1 Initial Selection

Selection of phages binding to the RR120 antigen under application conditions was essentially performed as described in example 2.4, but using the following conditions during the selection of the phages in the immunotubes:

1. 0.6 g/l OMO-MA in 25 mM sodiumcarbonate pH 9.0 with 2% marvel (0.6+M(9))

2. 3 g/l OMO-MA in 25 mM sodiumcarbonate pH 9.0 with 2% marvel (3+M(9))

3. 6 g/l OMO-MA in 25 mM sodiumcarbonate pH 9.0 with 2% marvel (6+M(9))

4. 6 g/l OMO-MA in 25 mM sodiumcarbonate pH 9.0 (6 (9))

5. 0.6 g/l LAS in 25 mM sodiumcarbonate pH 9.0 with 2% marvel (0.6 L+M(9))

6. 0.6 g/l LAS in 25 mM sodiumcarbonate pH 10.3 with 2% marvel (0.6 L+M(10.3))

7. 3 g/l OMO-MA in water with 2% marvel (3+M(10.3))

The results after three rounds of panning are presented in the following table 8

| Conditions | round 1 | Round 2 | round 3 |
| --- | --- | --- | --- |
| 1 0.6 + M(9) | 1 10⁴ | 4 10³ | — |
| 2 3 + M(9) | 1 10⁴ | 4 10³ | — |
| 3 6 + M(9) | 5 10³ | 8 10³ | — |
| 4 6 (9) | 12 | — | — |
| 5 0.6 L + M(9) | 1 10⁵ | 2 10⁶ | 8 10⁴ |
| 6 0.6 L + M(10.3) | 1 10⁵ | 1 10⁶ | 8 10⁴ |
| 7 3 + M(10.3) | 3 10⁵ | 7 10⁵ | 4 10⁴ |
| 8 PBS + M | 1 10⁵ | 5 10⁵ | 8 10⁴ |

As a comparison the results of the panning in PBS (see I.1) and 2% marvel are included.

IX.4.2 Screening of Free VHH Domains Produced by Selected Clones Under Application Conditions.

The fragments indicated in FIG. 10, and Table 9 were selected for further investigation

TABLE 9

| | Selection conditions |
| --- | --- |
| α-RR120 $V_{HH}$ | Selection |
| A38, A44 | PBS pH 7.4 |
| A306 | 0.6 g l⁻¹ LAS pH 9 (25 mM NaCO₃-buffer) |
| A307, A308 | 0.6 g l⁻¹ LAS pH 10.3 (25 mM NaCO₃-buffer) |
| A309 | 3 g l⁻¹ OMO pH 10.3 (water) |

After purification via ion exchange chromatography, the fragments were subjected to an ELISA assay according to the following approach:

An ELISA was performed using serial dilutions (in PBS) of the selected α-RR120 antibody fragments resulting in a set of standard dilution curves. The OD 450 nm signal was plotted against the log antibody concentration. The concentration at halve the maximal OD (450) is defined as the midpoint concentration and set as 100% immunoreactivity for the standard curve. Subsequently this experiment was repeated using serial dilutions made in product formulations at different concentrations. Again the immunoreactivity was determined (VHH concentration resulting in half the max OD450 achieved in that particular product concentration).

Figure 8:
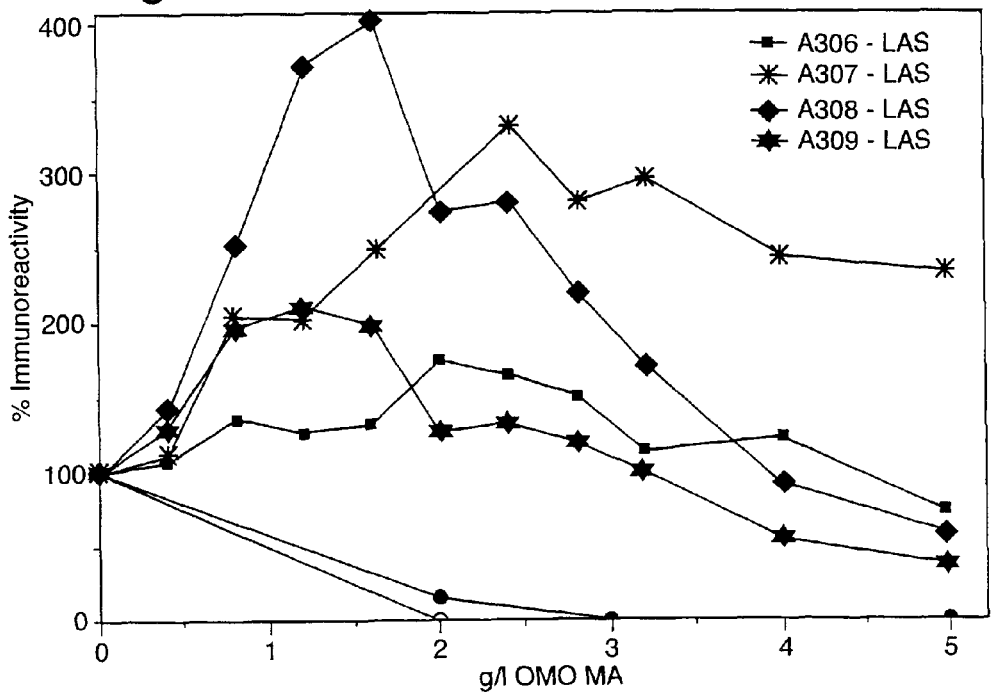
FIG. 8 shows the influence of different levels of OMO (without protease) on the stability of anti-RR120 VHHs in 25 mM NaCO3 and pH 10.3, whereby the amount of binding in 25 mM NaCO3 at pH 10.3 is set at 100% immunoreactivity.
Figure 9:
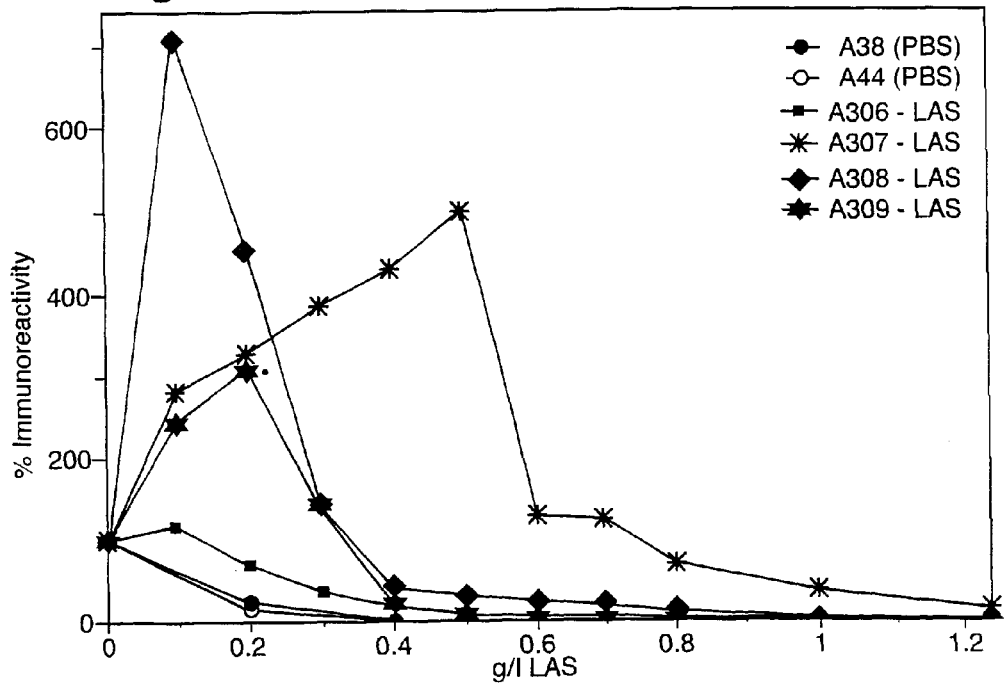
FIG. 9 shows the influence of different levels of LAS on the stability of anti-RR120 VHHs in 25 mM NaCO3 and pH 10.3, whereby the amount of binding in 25 mM NaCO3 at pH 10.3 is set at 100% immunoreactivity.

The relative immunoreactivity of the dilution curves in different product concentrations was then expressed as a percentage of the 100% immunoreactivity as determined from the standard curve and represented in FIGS. 8 and 9.

$$\% \text{ immunoreactivity} = \frac{\text{mid-point standard conditions}}{\text{mid-point application conditions}} \times 100$$

IX. 4.3 Sequences of VHH Domains which Bind to RR120 Under Application Conditions FIG. 10 represents the sequences of VHH domains which bind to RR120 under the conditions as described above.

LITERATURE REFERRED TO IN THE EXAMPLES

Bokhout, B. A., Van Gaalen, C., and Van Der Heijden, Ph. J., (1981), A selected water-in-oil emulsion: composition and usefulness as an immunological adjuvant. Vet. Immunol. Immunopath., 2:491-500

Bokhout, B. A., Bianchi, A. T. J., Van Der Heijden, Ph. J., Scholten, J. W. and Stok, W., (1986), The influence of a water-in-oil emulsion on humoral immunity. Comp. Immun. Microbiol. Infect. Dis., 9:161-168.

Chomczynnski, P. and Sacchi, N. (1987) Single step method of RNA isolation by acid guanidium thiocyanate-phenol-chloroform extraction. Analytical Biochem. 162:156-159.

Dente, L., Cesareni, G., Cortese, R. (1983) pEMBL—A new family of single stranded plasmids Nucleic Acids Research 11:1645-1655.

Faber, K. N., Haima, P., Harder, W., Veenhuis, M. and Geert, A. B., (1994) Highly efficient electrotransformation of the yeast Hansenula polymorpha. Current Genetics, 25: 305-310

Fernandes, P. M. B., Panek, A. D., and Kurtenbach, E. (1997) Effect of hydrostatic pressure on a mutant of Saccharomyces cerevisiae deleted in the trehalose-6-phosphate synthase gene. FEMS Microbiolology letters 152:17-21.

Friedberg, E. C., Siede, W. and Cooper, A. J. (1991) Cellular responses to DNA damage in yeast pp 147-192 in: The Molecular and Cellular Biology of the Yeast *Saccharomyces cerevisiae*. Eds. Broach, J. R, Pringel, J. R and Jones, E. W. Cold Spring Harbor Laboratory Press.

Giuseppin, M. L. F., Almkerk, J. W., Heistek, J. C., Verrips, C. T., (1993) Comparative Study on the Production of Guar Alpha-Galactosidase by *Saccharomyces cerevisiae* SU50B and *Hansenula polymorpha* 8/2 in Continuous Cultures. Applied and Environmental Microbiology 59:52-59.

Giuseppin, M. L. F., Lopes, M. T. S., Planta, R. J., Verbakel, J. M. A., Verrips, C. T. (1991) Process for preparing a protein by a yeast transformed by multicopy integration of an expression vector. PCT application WO 91/00920 (UNILEVER)

Harmsen, M. M., Langedijk, A. C., van Tuinen, E., Geerse, R. H., RauP, H. A., Maat, J., (1993) Effect of pmr1 disruption and different signal sequences on the intracellular processing and secretion of *Cyamopsis tetragonoloba*-galactosidase by *S. cerevisiae*. Gene 125 115-123

Hodgkins, M., Mead, D., Ballance, D. J., Goodey, A. and Sudbery, P., (1993) Expression of the Glucose Oxidase Gene from *Aspergillus niger* in *Hansenula Polymorpha* and its use as a reporter gene to isolate regulatory mutations. Yeast, 9:625-635

Klis, F. M., Schreuder, M. P., Toschka, H. Y. and Verrips, C. T., (1994) Process for immobilising enzymes to the cell wall of a microbial cell by producing a fusion protein. PCT application WO 94/01567 (UNILEVER)

Marks J. D., Hoogenboom H. R., Bonnert T. P., et al. (1991) By-passing immunization—Human-antibodies from V-gene libraries displayed on phage: Journal of Molecular Biology 222: (3) 581-597 Dec. 5, 1991

Mendoza-Vega, O., Sabatie, J, & Brown, S. W. (1994) Industrial-production of heterologous proteins by fed-batch cultures of the yeast *Saccharomyces cerevisiae*. FEMS Microbiology Reviews 15:369-410.

Piper, P., Mahe, Y., Thompson, S., Pandjaitan, R., Holyoak, C., Egner, R., Muhlbauer M., Coote P. and Kuchler, K. (1998) The pdr12 ABC transporter is required for the development of weak organic acid resistance in yeast. EMBO J. 17:4257-4265.

Tsukamoto, Y., Kato, J. and Ikeda, H., (1997) Silencing Factors participate in DNA-Repair and Recombination in *Saccharomyces cerevisiae*. Nature 388:900-903.

Van der Vaart, J. M. and C. T. Verrips (1998), Cell wall proteins of *S. cerevisiae*, Biotechnology and Genetic Engineering Reviews 15:387-411.

Wouters, P. C., Glaasker, E., Smelt, J. P. P. M., (1998) Effects of high pressure on inactivation kinetics and events related to proton efflux in *Lactobacillus plantarum* Applied And Environmental Microbiology 64:509-514.

Zijderveld, F. G. et al., (1990) Epitope analysis of the F4 (K88) fimbrial antigen complex of enterotoxigenic *E. coli* using monoclonal antibodies. Infection and Immunity, 58:1870-1878.

The invention claimed is:

1. A method of preparing a product, the method comprising:
   (i) identifying a VHH antibody that retains:
      (a) at least 70% of its original antigen binding activity following incubation at 80° C. for two hours, and
      (b) functional activity following exposure to the gastrointestinal tract of an animal; and
   (ii) incorporating into the products the VHH antibody identified in step (i).

2. The method according to claim 1, wherein the VHH antibody is derived from a natural source of VHH antibodies.

3. The method according to claim 1, wherein the VHH antibody retains at least 80% of its original antigen binding activity following incubation at 80° C. for two hours.

4. The method according to claim 1, wherein the product is an animal feed.

5. The method according to claim 1, wherein the product is orally administered.

6. The method according to claim 5, wherein the VHH antibody has binding activity directed to a bacterium capable of causing a gastrointestinal tract infection.

7. The method of claim 6, wherein the bacterium is *Escherichia coli*.

8. The method of claim 7, wherein the *Escherichia coil* is strain K88.

9. The method according to claim 1, wherein the VHH antibody incorporated into the product is produced recombinantly.

10. A method of preparing a product comprising an identified, active VHH antibody, the method comprising adding the identified, active VHH antibody into the product, wherein the active VHH antibody is selected and produced by a method comprising:
- (i) exposing a plurality of VHH antibodies to the gastrointestinal tract of an animal;
- (ii) identifying an active VHH antibody, wherein the identified, active VHH antibody retains antigen binding ability after exposure in (i);
- (iii) obtaining nucleic acid encoding the identified, active VHH antibody; and
- (iv) expressing the nucleic acid obtained in step (iii) to produce the identified, active VHH antibody.

11. The method according to claim 10, wherein the product is animal feed.

12. The method according to claim 10, wherein the product is orally administered.

13. The method according to claim 12, wherein the product VHH antibodies have binding activity directed to a bacterium capable of causing a gastrointestinal tract infection.

14. A method of preparing a product, the method comprising:
- (i) identifying a VHH antibody that retains functional activity following exposure to the gastrointestinal tract of an animal; and
- (ii) incorporating into the product the VHH antibody identified in step (0.

15. The method according to claim 14, wherein the product is orally administered.

16. The method according to claim 15, wherein the VHH antibody has binding activity directed to a bacterium capable of causing a gastrointestinal tract infection.

17. The method according to claim 14, wherein the VHH antibody incorporated into the product is produced recombinantly.

* * * * *

UNITED STATES PATENT AND TRADEMARK OFFICE
CERTIFICATE OF CORRECTION

| | | |
|---|---|---|
| PATENT NO. | : 9,080,157 B2 | Page 1 of 1 |
| APPLICATION NO. | : 13/462262 | |
| DATED | : July 14, 2015 | |
| INVENTOR(S) | : Daniel Convents et al. | |

It is certified that error appears in the above-identified patent and that said Letters Patent is hereby corrected as shown below:

In the Claims

Column 46, line 10, "step (0." should read --step (i).--.

Signed and Sealed this
Seventeenth Day of November, 2015

Michelle K. Lee
*Director of the United States Patent and Trademark Office*